(12) United States Patent
Guzaev et al.

(10) Patent No.: US 6,653,468 B1
(45) Date of Patent: Nov. 25, 2003

(54) UNIVERSAL SUPPORT MEDIA FOR SYNTHESIS OF OLIGOMERIC COMPOUNDS

(75) Inventors: Andrei P. Guzaev, Vista, CA (US); Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/260,076

(22) Filed: Sep. 30, 2002

Related U.S. Application Data

(60) Provisional application No. 60/400,312, filed on Jul. 31, 2002.

(51) Int. Cl.⁷ .......................... C07H 21/00; C07F 9/02
(52) U.S. Cl. .............................. 536/25.31; 536/25.3
(58) Field of Search .......................... 536/25.31, 25.3

(56) References Cited

U.S. PATENT DOCUMENTS

| | | | | |
|---|---|---|---|---|
| 5,869,696 | A | | 2/1999 | Reddy et al. ............... 548/564 |
| 5,886,193 | A | * | 3/1999 | McLean et al. ............. 548/544 |
| 6,166,239 | A | * | 12/2000 | Manoharan ................ 558/268 |
| 6,294,664 | B1 | * | 9/2001 | Ravikumar et al. ........ 536/25.3 |
| 6,310,198 | B1 | * | 10/2001 | Tang et al. ................. 536/25.3 |
| 6,429,309 | B1 | * | 8/2002 | Kwiatkowski et al. ..... 536/25.3 |

OTHER PUBLICATIONS

Azhayev, A.V., "A new universal solid support for oligonucleotide synthesis," *Tetrahedron*, 1999, 55, 787–800.

Azhayev, A.V., et al., "Amide group assisted 3'–dephosphorylation of oligonucleotides synthesized on universal A–supports," *Tetrahedron*, 2001, 57, 4997–4986.

Besecke, S., et al., "Bicycloheptenedicarboxylic anhydride derivative polymers," Priority Appln. Information, DE 1991–4117369, *SciFinder*, Aug. 29, 2002, 2 pages (abstract only).

Crea, R., et al., "Synthesis of oligonucleotides on cellulose by a phosphotriester method," *Nucleic Acids Research*, Jan. 22, 1980, 8(10), 2331–2348.

Lyttle, M.H., et al., "A new universal linker for solid phase DNA synthesis," *Nucleic Acids Research*, 1996, 24(14), 2793–2798.

Lyttle, M.H., et al., "A phosphate bond universal linker for DNA synthesis," *Nucleosides & Nucleotides*, 1999, 18(8), 1809–1824.

McCluskey, A., et al., "The first two cantharidin analogues displaying PP1 selectivity," *SciFinder*, Aug. 29, 2002, 3 pages (abstract only).

Nelson, P.S., et al., "3'–terminal modification of oligonucleotides using a universal solid support," *Nucleosides & Nucleotides*, 1997, 16(10&11), 1951–1959.

Nelson, P.S., "Rainbow™ universal CPG: A versatile support for oligonucleotide synthesis," *Bio Techniques*, 1997, 22, 752–756.

Scheuer–Larsen, C., et al., "Introduction of a universal solid support for oligonucleotide synthesis," *Nucleosides & Nucleotides*, 1997, 16(1&2), 67–80.

Schwartz, M.E., et al., "A universal adapter for chemical synthesis of DNA or RNA on any single type of solid support," *Pergamon*, Nov. 2, 1994, 27–30.

Scott, S., et al., "A universal support for oligonucleotide synthesis," *Innovation and Perspectives in Solid Phase Synthesis*, Epton, R. (Ed.), 1994, 115–124.

Reg. No. 41532–47–2 "Isobenzofuran–4,7–imine–1,3–dione,3a,4,7,7a–tetrahydro–8–methyl–(9CI)," *SciFinder*, Aug. 29, 2002 2 pages (abstract only).

Reg. No. 99237–90–8 Isobenzofuran–4,7–imine–1,3–dione, 8–acetyl–3a,4,7,7a–tetrahydro–,(3aα,4a,7a,7 aα)–(9CI), *SciFinder*, Aug. 29, 2002 2 pages (abstract only).

\* cited by examiner

*Primary Examiner*—Deborah C. Lambkin
(74) *Attorney, Agent, or Firm*—Woodcock Washburn LLP

(57) ABSTRACT

Compounds for the synthesis of oligomeric compounds, particularly oligonucleotides and oligonucleotide mimetics, are provided. In addition, methods for functionalizing a support medium with a first monomeric subunit and methods for the synthesis of oligomeric compounds utilizing the novel compounds bound to support media are provided.

40 Claims, No Drawings

UNIVERSAL SUPPORT MEDIA FOR SYNTHESIS OF OLIGOMERIC COMPOUNDS

This application claims benefit of Provisional application No. 60/400,312 filed Jul. 31, 2002.

FIELD OF THE INVENTION

This invention is directed in one aspect to compounds useful in the preparation of novel universal support media. The universal support media thus prepared are useful in the preparation of oligomeric compounds.

BACKGROUND OF THE INVENTION

Support bound oligonucleotide synthesis relies on sequential addition of nucleotides to one end of a growing chain. Typically, a first nucleoside is attached to an appropriate support medium such as a glass bead support and activated phosphorus compounds (typically nucleotide phosphoramidites, also bearing appropriate protecting groups) are added stepwise to elongate the growing oligonucleotide. When the chain elongation is completed, the oligonucleotide is cleaved from its support and protecting groups are removed. Additional methods for support bound synthesis methods may be found in Caruthers U.S. Pat. Nos. 4,415,732; 4,458,066; 4,500,707; 4,668,777; 4,973,679; and 5,132,418; and Koster U.S. Pat. No. 4,725,677 and U.S. Re. Pat. No. 34,069.

In carrying out standard oligonucleotide syntheses, workers minimally need to maintain a supply of eight different nucleoside-loaded supports for DNA and RNA syntheses, each prederivatized with a separate nucleoside corresponding to the 3' terminus of the desired oligomer (adenosine, guanosine, cytidine, uridine, deoxyadenosine, deoxyguanosine, deoxycytidine, and thymidine). If a modified nucleoside is desired at the 3'-terminus then additional prederivatized supports are required. Typically, the first nucleoside is covalently bound by a succinate or hydroquinone-O,O'-diacetate linker. Furthermore, certain oligonucleotides with unusual nucleosides are available only as phosphoroamidites but not as supports.

A universal support is a support that may be used as a starting point for oligonucleotide synthesis regardless of the nucleoside species at the 3' end of the sequence. A universal support has broad application and remedies the aforementioned deficiencies of standard oligonucleotide synthesis procedures because only one support is needed to carry out the oligonucleotide synthesis regardless of what base is desired at the 3' end. This simplifies the synthetic strategy, reduces the number of required reagents in inventory and reduces the likelihood of errors in parallel synthesis applications.

Some researchers have employed derivatized glass supports with 2'(3')-O-benzoyluridine 5'-O-succinyl so that the uridine moiety is linked to the glass via a succinate linkage [deBear et al., Nucleosides and Nucleotides 6, 821–830 (1987)]. Oligonucleotide synthesis takes place by adding nucleotide monomers to the 2' or 3' position of the uridine. Following the synthesis, the newly synthesized oligonucleotide is released from the glass, deprotected and cleaved from the uridinyl terminus in one reaction. Since it is cleaved from the solid support in the cleaving reaction, the uridinyl functionality is no longer available for subsequent oligonucleotide syntheses.

In a similar approach, Crea et al. prepared the dimer 5'-O-p-chlorophenylphospho-2'(3')-O-acetyluridinyl-[2'-(3')-3']-5'-O-dimethoxytritylthymidine p-chlorophenylester and attached the dimer to cellulose via a phosphate linkage. The 5' position of the thymidine is available for oligonucleotide attachment and synthesis. [Crea et al., Nucleic Acids Research 8, 2331 (1980)]. Aqueous concentrated ammonia is used to the release of the synthesized oligonucleotide from the cellulose leaving the uridine portion of the dimer attached to the cellulose. Although Crea et al. utilized the reactive vicinal groups on the uridine as the release site for the oligonucleotide from the uridine the solid support suggested in this reference is not truly a universal solid support because the 3'-terminal oligonucleotide is incorporated in the solid support reagent and a different support is required for oligonucleotides incorporating a different first nucleoside.

Schwartz et al. attached an adapter, 2'-(3')-O-dimethoxytrityl-3'-(2')-O-benzoyluridine-5'-O-(2-cyanoethyl-N,N-diisopropylphosphoramidite, to a thymidine derivatized polystyrene and synthesized an oligonucleotide from the O-dimethoxytrityl position of the uridine [Schwartz et al., Tetrahedron Letters, 36, 1, 27–30, 1995]. While this approach provides a universal solid support for oligonucleotide synthesis, cleavage releases both the adapter and the thymidine from the support and then the synthesized oligonucleotide from the uridine. Thus, thymidine linker must be removed as an impurity and the solid support is unavailable for subsequent reactions.

Some universal supports require cleavage under conditions supplemental to ammonium hydroxide, [Lyttle et al., Nucleic Acids Research, 1996, 24, 14, 2793–2798] making them less useful in many conventional syntheses where ammonium hydroxide is used as cleavage reagent.

The compounds, compositions and processes of the invention provide novel universal support media useful for preparing oligomeric compounds, including oligonucleotides and oligonucleotide mimetics, which may be effectively cleaved without rendering the support media unavailable for subsequent reactions.

BRIEF SUMMARY OF THE INVENTION

In one embodiment, the invention is directed to compounds of Formula I:

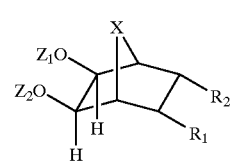

wherein
X is $CH_2$, O, S or $NR_3$;
$R_3$ is alkyl, —C(=O)alkyl or an amino protecting group;
one of $R_1$ and $R_2$ is —(L)$_n$-sm and the other of $R_1$ and $R_2$ is —C(=O)—$R_4$ or —C(=S)—$R_4$;
L is a linking moiety;
n is 0 or 1;
sm is a support medium;
$R_4$ is —O-alkyl, —N($J_1$)$J_2$;
$J_1$ is H or alkyl;
$J_2$ is alkyl or a nitrogen-protecting group;
or $J_1$ and $J_2$ together with the nitrogen atom they are attached to form a ring structure; and
$Z_1$ and $Z_2$ are orthogonal hydroxyl protecting groups.

Preferably, X is O, S or $NR_3$. Preferably, $R_3$ is alkyl or —C(=O)alkyl. More preferably, X is O; and one of $R_1$ and $R_2$ is —$(L)_n$-sm and the other of $R_1$ and $R_2$ is —C(=O)—$R_4$. Preferably, L is —C(=O)—. Preferably, $R_4$ is —N(H)alkyl or N-piperidinyl. More preferably, $Z_1$ is —C(=O)$CH_3$; and $Z_2$ is dimethoxytrityl.

The support medium may be a controlled pore glass, oxalyl-controlled pore glass, silica-containing particles, polymers of polystyrene, copolymers of polystyrene, copolymers of styrene and divinylbenzene, copolymers of dimethylacrylamide and N,N'-bisacryloylethylenediamine, soluble support medium or PEPS.

$Z_1$ may be a trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, 9-fluorenylmethoxycarbonyl, levulinyl or acetoacetyl groups.

$Z_2$ may be a 4,4'-dimethoxytrityl (DMT), monomethoxytrityl, 9-phenylxanthen-9-yl (Pixyl), 9-(p-methoxyphenyl)xanthen-9-yl (Mox), t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetyl, chloroacetyl, trichloroacetyl, trifluoroacetyl, pivaloyl, benzoyl, p-phenylbenzoyl, mesyl, tosyl, 4,4',4"-tris-(benzyloxy)trityl (TBTr), 4,4',4"-tris-(4,5-dichlorophthalimido)trityl (CPTr), 4,4',4"-tris(levulinyloxy)trityl (TLTr); 3-(imidazolylmethyl)-4,4'-dimethoxytrityl (IDTr), 4-decyloxytrityl ($C_{10}$Tr), 4-hexadecyloxytrityl ($C_{16}$Tr), 9-(4-octadecyloxyphenyl)xanthene-9-yl ($C_{18}$Px), 1,1-bis-(4-methoxyphenyl)-1'-pyrenyl methyl (BMPM), p-phenylazophenyloxycarbonyl (PAPoc), 9-fluorenylmethoxycarbonyl (Fmoc), 2,4-dinitrophenylethoxycarbonyl (DNPEoc), 4-(methylthiomethoxy)butyryl (MTMB), 2-(methylthiomethoxymethyl)-benzoyl (MTMT), 2-(isopropylthiomethoxymethyl)benzoyl (PTMT), 2-(2,4-dinitrobenzenesulphenyloxymethyl) benzoyl (DNBSB), or levulinyl groups.

In another embodiment, the invention is directed to a method for functionalizing a support medium with a first monomeric subunit, comprising the steps of:

providing a support bound compound of Formula I:

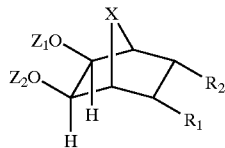

wherein
X is $CH_2$, O, S or $NR_3$;
$R_3$ is alkyl, —C(=O)alkyl or an amino protecting group;
one of $R_1$ and $R_2$ is —$(L)_n$-sm and the other of $R_1$ and $R_2$ is —C(=O)—$R_4$ or —C(=S)—$R_4$;
L is a linking moiety;
n is 0 or 1;
sm is a support medium;
$R_4$ is —O-alkyl, —N($J_1$)$J_2$;

$J_1$ is H or alkyl;
$J_2$ is alkyl or a nitrogen protecting group;
or $J_1$ and $J_2$ together with the nitrogen atom to which they are attached form a ring structure; and
$Z_1$ and $Z_2$ are orthogonal hydroxyl protecting groups;
selectively deblocking one of said orthogonal hydroxyl protecting groups to give a reactive hydroxyl group; and
treating said reactive hydroxyl group with a first monomeric subunit having an activated phosphorus group and a further protected hydroxyl group thereon for a time and under conditions sufficient to form a monomer-functionalized support medium.

In certain embodiments, the method may further comprise the steps of:
treating said monomer-functionalized support medium with a capping agent; and
optionally, treating said monomer-functionalized support medium with an oxidizing agent.

In other embodiments, the method includes the further steps of:
deblocking said further protected hydroxyl group to give a reactive hydroxyl group;
treating the reactive hydroxyl group with a further monomeric subunit having an activated phosphorus group and a further protected hydroxyl group thereon for a time and under conditions sufficient to form an extended compound;
treating said extended compound with a capping agent;
optionally, treating said extended compound with an oxidizing or sulfurizing agent;
repeating the preceding four steps one or more times to form a further extended compound; and
treating said further extended compound with an oxidizing or sulfurizing agent to form an oligomeric compound.

In certain embodiments, said last treating step cleaves said oligomeric compound from said support medium. Preferably, said last treating step is effective to remove protecting groups present on said oligomeric compound. Preferably, said cleaved oligomeric compound has a terminal hydroxyl group at the site of cleavage and, more preferably, said terminal hydroxyl group is attached to a 2'- or 3'-position of a nucleoside that is located at the 3'-terminus of said oligomeric compound.

In certain other embodiments, the process further comprises the step of treating said oligomeric compound with a reagent effective to cleave said oligomeric compound from said support medium. Preferably, said treating step is effective to remove protecting groups present on said oligomeric compound. Preferably, said cleaved oligomeric compound has a terminal hydroxyl group at the site of cleavage and, more preferably, said terminal hydroxyl group is attached to a 2'- or 3'-position of a nucleoside that is located at the 3'-terminus of said oligomeric compound.

Preferably, the treating step of said reactive hydroxyl group with a monomeric subunit having an activated phosphorus group and a further protected hydroxyl is performed in the presence of an activating agent.

Preferably, said monomeric subunit having an activated phosphorus group is a phosphoramidite, an H-phosphonate or a phosphate triester.

Preferably, said hydroxyl protecting group $Z_1$ and each of said further hydroxyl protecting groups are acid labile.

In certain preferred embodiments of the process, said hydroxyl protecting group $Z_1$ and each of said further hydroxyl protecting groups are removed by contacting said hydroxyl protecting groups with an acid, wherein the acid is formic acid, acetic acid, chloroacetic acid, dichloroacetic acid, trichloroacetic acid, trifluoroacetic acid, benzenesulfonic acid, toluenesulfonic acid, or phenylphosphoric acid.

Preferably, the oligomeric compounds may be oligonucleotides, modified oligonucleotides, oligonucleotide analogs, oligonucleosides, oligonucleotide mimetics, hemimers, gapmers and chimeras.

DETAILED DESCRIPTION OF THE INVENTION

The present invention provides compounds and processes useful for the support mediated synthesis of oligomeric compounds. Compounds of the invention are initially attached to support media and subsequently deblocked thereby providing a free hydroxyl group. This free hydroxyl group is used for oligomer synthesis in an analogous manner to the free 5'-hydroxyl group that is provided when using a nucleoside derivatized commercially supplied support medium. In one embodiment, the free hydroxyl group of the universal support medium free may be reacted with a monomeric subunit having an activated phosphorus group to form a phosphite linkage. The synthesis continues in this manner iteratively until the desired oligomeric compound is prepared. The traditional iterative steps include oxidation, capping and deblocking. When the desired sequence has been iteratively synthesized, the oligomeric compound is cleaved from the support media leaving a terminal hydroxyl group attached to the oligomeric compound where the initial phosphite linkage attached the first monomeric subunit to the support medium.

As used herein, the term "orthogonally protecting groups" refers to functional groups that are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in, for example, automated oligonucleotide synthesis. A functional group is deblocked in the presence of one or more other protected functional groups that is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In the context of this invention, the term "oligomeric compound" refers to a polymeric structure capable of being prepared using well-known support mediated synthetic methods. Preferred oligomeric compounds are also capable of hybridizing a region of a nucleic acid molecule. The term includes oligonucleotides, oligonucleosides, oligonucleotide analogs, modified oligonucleotides, oligonucleotide mimetics, hemimers, gapmers and chimeras. Oligomeric compounds can be prepared to be linear or circular and may include branching. They can be prepared single stranded or double stranded and may include overhangs. In general, an oligomeric compound comprises a backbone of linked momeric subunits where each linked momeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds, including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The terms "oligonucleotide analog" and "modified oligonucleotide" refers to oligonucleotides that have one or more non-naturally occurring portions which function in a similar manner to oligonulceotides. Such modified or substituted oligonucleotides are often preferred over native forms because of desirable properties such as, for example, enhanced cellular uptake, enhanced affinity for nucleic acid target and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In the context of this invention, the term "oligonucleotide mimetic" refers to an oligonucleotide wherein the backbone of the nucleotide units has been replaced with novel groups. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

One class of oligonucleotide mimetic that has been reported to have excellent hybridization properties is peptide nucleic acids (PNA). The backbone in PNA compounds is two or more linked aminoethylglycine units that give PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

PNA has been modified to incorporate numerous modifications since the basic PNA structure was first prepared. The basic structure is shown below:

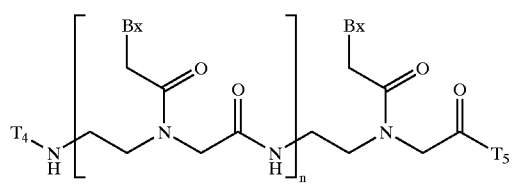

wherein

Bx is a heterocyclic base moiety;

$T_4$ is is hydrogen, an amino protecting group, —C(O)R$_5$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are hydroxyl, amino, alkoxy, carboxy, benzyl, phenyl, nitro, thiol, thioalkoxy, halogen, alkyl, aryl, alkenyl or alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$–$C_6$ alkyl, or an amino protecting group;

$Z_2$ is hydrogen, $C_1$–$C_6$ alkyl, an amino protecting group, —C(=O)—(CH$_2$)$_n$—J—Z$_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —C$_1$–C$_6$ alkyl, —C(=O)—CH$_3$, benzyl, benzoyl, or —(CH$_2$)$_n$—N(H)Z$_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups has been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides that are less likely to form undesired interactions with cellular proteins (Dwaine A. Braasch and David R. Corey, *Biochemistry*, 2002, 41(14), 4503–4510). Morpholino-based oligomeric compounds are disclosed in U.S. Pat. No. 5,034,506, issued Jul. 23, 1991. The morpholino class of oligomeric compounds has been prepared having a variety of different linking groups joining the monomeric subunits.

Morpholino nucleic acids have been prepared having a variety of different linking groups ($L_2$) joining the monomeric subunits. The basic formula is shown below:

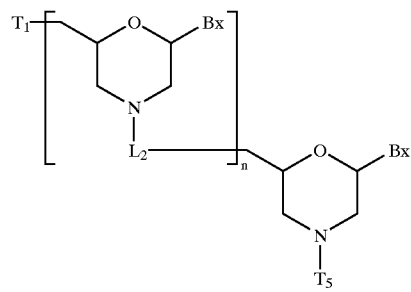

wherein:

$T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595–8602). In general the the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

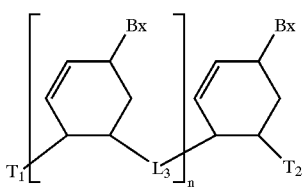

wherein:
each Bx is a heterocyclic base moiety;
T₁ is hydroxyl or a protected hydroxyl; and
T₂ is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563–1566) and would have the general formula:

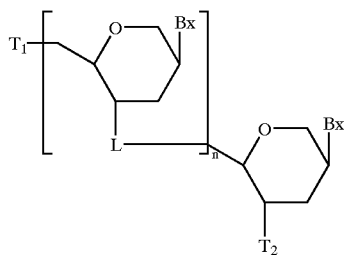

A further prefered modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methelyne (—CH₂—)ₙ group bridging the 2' oxygen atom and the 4' carbon atom wherein n is 1 or 2 (Singh et al., Chem. Commun., 1998, 4, 455–456). LNA and LNA analogs display very high duplex thermal stabilities with complementary DNA and RNA (Tm=+3 to +10 C), stability towards 3'-exonucleolytic degradation and good solubility properties. The basic structiure of LNA showing the bicyclic ring system is shown below:

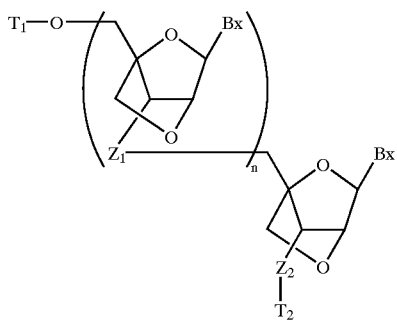

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., *J. Mol. Recognit.*, 2000, 13, 44–53). These conformations are associated with improved stacking of the nucleobases (Wengel et al., *Nucleosides Nucleotides*, 1999, 18, 1365–1370).

LNA has been shown to form exceedingly stable LNA:LNA duplexes (Koshkin et al., J. Am. Chem. Soc., 1998, 120, 13252–13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (especially LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-modified oligonucleotides, as well as the LNAs, are useful in a wide range of diagnostic and therapeutic applications. Among these are antisense applications, PCR applications, strand-displacement oligomers, substrates for nucleic acid polymerases and generally as nucleotide-based drugs.

Potent and nontoxic antisense oligonucleotides containing LNAs have been described (Wahlestedt et al., *Proc. Natl. Acad. Sci. U.S.A.*, 2000, 97, 5633–5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607–3630). LNAs and preparation thereof are also described in WO 98/39352 and WO 99/14226.

The first analogs of LNA, phosphorothioate-LNA and 2'-thio-LNAs, have also been prepared (Kumar et al., *Bioorg. Med. Chem. Lett.*, 1998, 8, 2219–2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., *J. Org. Chem.*, 1998, 63, 10035–10039). In addition, 2'-amino- and 2'-methylamino-LNAs have been prepared and the thermal stability of their duplexes with complementary RNA and DNA strands has been previously reported.

Further oligonucleotide mimetics have been prepared to incude bicyclic and tricyclic nucleoside analogs having the formulas (amidite monomers shown):

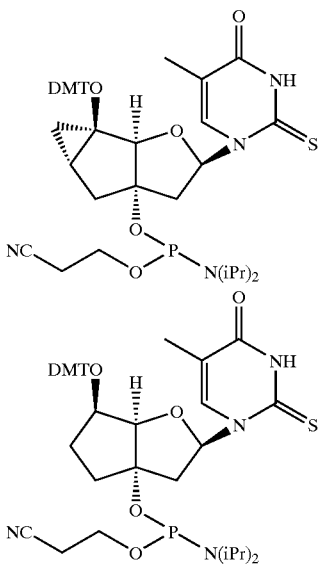

(see Steffens et al., *Helv. Chim. Acta*, 1997, 80, 2426–2439; Steffens et al., *J. Am. Chem. Soc.*, 1999, 121, 3249–3255; and Renneberg et al., *J. Am. Chem. Soc.*, 2002, 124, 5993–6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

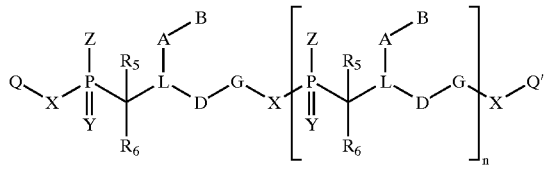

Another oligonucleotide mimetic has been reported wherein the furanosyl ring has been replaced by a cyclobutyl moiety.

The internucleotide linkage found in native nucleic acids is a phosphodiester linkage. This linkage has not been the linkage of choice for synthetic oligonucleotides that are for the most part targeted to a portion of a nucleic acid such as mRNA because of stability problems e.g. degradation by nucleases. Preferred internucleotide linkages and internucleoside linkages as is the case for non phosphate ester type linkages include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleoside linkages is a 3' to 3', 5' to 5' or 2' to 2' linkage. Preferred oligonucleotides having inverted polarity comprise a single 3' to 3' linkage at the 3'-most internucleotide linkage, i.e. a single inverted nucleoside residue that may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=(O)(OH))—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Oligomeric compounds can have a variety of substituent groups attached at various positions. Furanosyl groups found in native nucleic acids as well as various oligomeric compounds can be substituted at a number of positions. The most frequently substituted position is the 2'-position of ribose. The 3', 4', and 5' have also been substituted with substituent groups generally referred to as sugar substituent groups. Preferred sugar substituent groups include: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other sugar substituent groups include: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

More preferred sugar substituent groups that are more frequently covalently attached to the 2'-sugar position include methoxyethoxy (—O—CH$_2$CH$_2$OCH$_3$, also known as —O—(2-methoxyethyl) or MOE) (Martin et al., *Helv. Chim. Acta*, 1995, 78, 486–504), i.e., an alkoxyalkoxy group. A further preferred 2'-modification includes dimethylaminooxyethoxy, i.e., a —O(CH$_2$)$_2$ON(CH$_3$)$_2$ group, also known as DMAOE, as described in examples hereinbelow, and -dimethylaminoethoxyethoxy (also known in the art as —O-dimethylaminoethoxyethyl or -DMAEOE), i.e., O—CH$_2$—O—CH$_2$—N(CH$_2$)$_2$, also described in examples hereinbelow.

Other preferred sugar substituent groups that are more frequently covalently attached to the 2'-sugar position include methoxy (—O—CH$_3$), aminopropoxy (—OCH$_2$CH$_2$CH$_2$NH$_2$), allyl (—CH$_2$—CH=CH$_2$)), —O-allyl (—O—CH$_2$—CH=CH$_2$) and fluoro (—F). A 2"-substituent group on a furanosyl ring can be in the ribo (down) or arabino (up) position. Preferred 2'-arabino modifications include fluoro and hydroxy. Similar modifications may also be made at other positions on an oligomeric compound, particularly the 3' position of the sugar for a 2'–5' linked oligomeric compound, the 3'-terminus and the 5'-position of the 5'-terminus. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic comounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

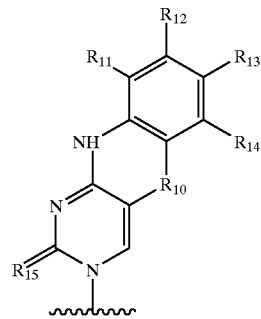

Representative cytosine analogs that make 3 hydrogen bonds with a guanosine in a second strand include 1,3-diazaphenoxazine-2-one (R$_{10}$=O, R$_{11}$–R$_{14}$=H) [Kurchavov, et al., *Nucleosides and Nucleotides*, 1997, 16, 1837–1846], 1,3-diazaphenothiazine-2-one (R$_{10}$=S, R$_{11}$–R$_{14}$=H), [Lin, K-Y; Jones, R. J.; Matteucci, M. J. Am. Chem. Soc. 1995, 117, 3873–3874] and 6,7,8,9-tetrafluoro-1,3-diazaphenoxazine-2-one (R$_{10}$=O, R$_{11}$–R$_{14}$=F) [Wang, J.; Lin, K-Y, Matteucci, M. Tetrahedron Lett. 1998, 39, 8385–8388]. Incorporated into oligonucleotides these base modifications were shown to hybridize with complementary guanine and the latter was also shown to hybridize with adenine and to enhance helical thermal stability by extended stacking interactions (also see U.S. Patent Application entitled "Modified Peptide Nucleic Acids" filed May 24, 2002, Serial number; and U.S. Patent Application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold (R$_{10}$=O, R$_{11}$=—O—(CH$_2$)$_2$—NH$_2$, R$_{12-14}$=H) [Lin, K.-Y.; Matteucci, M., *J. Am. Chem. Soc.* 1998, 120, 8531–8532]. Binding studies demonstrated that a single incorporation could enhance the binding affinity of a model oligonucleotide to its complementary target DNA or RNA with a $\Delta T^m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M., *J. Am. Chem. Soc.* 1998, 120, 8531–8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K-Y; Wagner, R. W.; Matteucci, M. *Proc. Natl. Acad. Sci. USA*, 1999, 96, 3513–3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos.: 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

A further preferred modification of oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937.

Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds that are chimeric compounds. "Chimeric" oligomeric compounds or "chimeras," in the context of this invention, are oligomeric compounds that contain two or more chemically distinct regions, each made up of at least one monomer unit, i.e., a nucleotide in the case of an oligonucleotide compound. These oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, modified oligonucleotides, oligonucleotide analogs, oligonucleosides and/or oligonucleotide mimetics as described above. Such compounds have also been referred to in the art as hybrids hemimers, gapmers or inverted gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyl-uracil and 5-propynyl-cytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'-O-methoxyethyl sugar modifications.

Further modified nucleobases include tricyclic heterocyclic base moieties such as for example 1,3-diazaphenoxazine-2-one (1H-pyrimido[5,4-b][1,4]benzoxazin-2(3H)-one) and G-clamps such as 9-(2-aminoethoxy)-1,3,-diazaphenoxazine-2-one. Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367, 066; 5,432,272; 5,457,187; 5,459,255; 5,484,908; 5,502, 177; 5,525,711; 5,552,540; 5,587,469; 5,594,121, 5,596, 091; 5,614,617; 5,645,985; 5,750,692; 5,830,653; 5,763, 588; 6,005,096; and 5,681,941, certain of which are commonly owned with the instant application, and each of which is herein incorporated by reference.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The reagents useful in the synthesis of oligomeric compounds have the structure of Formula I:

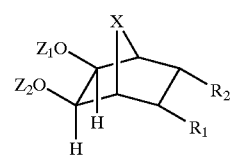

I wherein
X is $CH_2$, O, S or $NR_3$;
    $R_3$ is alkyl, —C(=O)alkyl or an amino protecting group;
one of $R_1$ and $R_2$ is —(L)$_n$-sm and the other of $R_1$ and $R_2$ is —C(=O)—$R_4$ or —C(=S)—$R_4$;
    L is a linking moiety;
    n is 0 or 1;
    sm is a support medium;
    $R_4$ is —O-alkyl, —N(J$_1$)J$_2$;
        $J_1$ is H or alkyl;
        $J_2$ is alkyl or a nitrogen-protecting group;
        or $J_1$ and $J_2$ together with the nitrogen atom they are attached to form a ring structure; and
    $Z_1$ and $Z_2$ are orthogonal hydroxyl protecting groups.
Preferably, X is O, S or $NR_3$. Preferably, $R_3$ is alkyl or —C(=O)alkyl. More preferably, X is O; and one of $R_1$ and $R_2$ is —(L)$_n$-sm and the other of $R_1$ and $R_2$ is —C(=O)—$R_4$. Preferably, L is —C(=O)—. Preferably, $R_4$ is —N(H)alkyl or N-piperidinyl. More preferably, $Z_1$ is —C(=O)CH$_3$; and $Z_2$ is dimethoxytrityl.

To prepare compounds of the invention wherein X is S or NR$_3$, one may begin with starting materials known to those of skill in the art, including the cantharidin analogues disclosed by McCluskey et al., *Bioorganic & Medicinal Chemistry Letters* (2002), 12(3), 391–393; the bicycloheptenedicarboxylic anhydride derivative polymers disclosed by Besecke et al. in German Application 91-4117369; isobenzofuran-4,7-imine-1,3-dione,3a,4,7,7a-tetrahydro-8- methyl (CA Registry No. 41532-47-2); and; isobenzofuran-4,7-imine-1,3-dione,8-acetyl-3a,4,7,7a-tetrahydro-, (3aα, 4α,7α,7aα)- (CA Registry No. 99237-90-8).

Preferably, the support medium is a controlled pore glass, oxalyl-controlled pore glass, silica-containing particles, polymers of polystyrene, copolymers of polystyrene, copolymers of styrene and divinylbenzene, copolymers of dimethylacrylamide and N,N'-bisacryloylethylenediamine, soluble support medium or PEPS.

Preferably, $Z_1$ is trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, 9-fluorenylmethoxycarbonyl, levulinyl or acetoacetyl groups.

Preferably, $Z_2$ is 4,4'-dimethoxytrityl (DMT), monomethoxytrityl, 9-phenylxanthen-9-yl (Pixyl), 9-(p-methoxyphenyl)xanthen-9-yl (Mox), t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetyl, chloroacetyl, trichloroacetyl, trifluoroacetyl, pivaloyl, benzoyl, p-phenylbenzoyl, mesyl, tosyl, 4,4',4"-tris-(benzyloxy)trityl (TBTr), 4,4',4"-tris-(4,5-dichlorophthalimido)trityl (CPTr), 4,4',4"-tris(levulinyloxy) trityl (TLTr); 3-(imidazolylmethyl)-4,4'-dimethoxytrityl (IDTr), 4-decyloxytrityl ($C_{10}$Tr), 4-hexadecyloxytrityl ($C_{16}$Tr), 9-(4-octadecyloxyphenyl)xanthene-9-yl ($C_{18}$Px), 1,1-bis-(4-methoxyphenyl)-1'-pyrenyl methyl (BMPM), p-phenylazophenyloxycarbonyl (PAPoc), 9-fluorenylmethoxycarbonyl (Fmoc), 2,4-dinitrophenylethoxycarbonyl (DNPEoc), 4-(methylthiomethoxy)butyryl (MTMB), 2-(methylthiomethoxymethyl)-benzoyl (MTMT), 2-(isopropylthiomethoxymethyl)benzoyl (PTMT), 2-(2,4-dinitrobenzenesulphenyloxymethyl)benzoyl (DNBSB), or levulinyl groups.

Other representative hydroxyl protecting groups commonly used in the art may be found in Beaucage, et al., *Tetrahedron* 1992, 48, 2223; and Greene and Wuts, *Protective Groups in Organic Synthesis*, Chapter 2, 2d ed, John Wiley & Sons, New York, 1991, each of which are hereby incorporated by reference in their entirety. Preferred protecting groups include dimethoxytrityl (DMT), monomethoxytrityl, 9-phenylxanthen-9-yl (Pixyl) and 9-(p-methoxyphenyl)xanthen-9-yl (Mox).

Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., *Protocols for Oligonucleotide Conjugates*, Eds, Humana Press; New Jersey, 1994; Vol. 26 pp. 1–72.

The methods of the invention are useful for functionalizing a support medium with a first monomeric subunit. In one embodiment, the method comprises the steps of:

providing a support bound compound of Formula I:

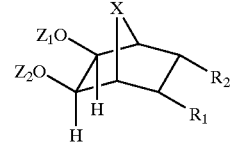

wherein
X is $CH_2$, O, S or $NR_3$;
$R_3$ is alkyl, —C(=O)alkyl or an amino protecting group;
one of $R_1$ and $R_2$ is —(L)$_n$-sm and the other of $R_1$ and $R_2$ is —C(=O)—$R_4$ or —C(=S)—$R_4$;
L is a linking moiety;
n is 0 or 1;
sm is a support medium;
$R_4$ is —O-alkyl, —N($J_1$)$J_2$;
$J_1$ is H or alkyl;
$J_2$ is alkyl or a nitrogen-protecting group;
or $J_1$ and $J_2$ together with the nitrogen atom to which they are attached form a ring structure; and
$Z_1$ and $Z_2$ are orthogonal hydroxyl protecting groups;
selectively deblocking one of said orthogonal hydroxyl protecting groups to give a reactive hydroxyl group; and
treating said reactive hydroxyl group with a first monomeric subunit having an activated phosphorus group and a further protected hydroxyl group thereon for a time and under conditions sufficient to form a monomer-functionalized support medium.

In certain embodiments, the method may further comprise the steps of:
treating said monomer-functionalized support medium with a capping agent; and
optionally, treating said monomer-functionalized support medium with an oxidizing agent.

In other embodiments, the method includes the further steps of:
deblocking said further protected hydroxyl group to give a reactive hydroxyl group;
treating the reactive hydroxyl group with a further monomeric subunit having an activated phosphorus group and a further protected hydroxyl group thereon for a time and under conditions sufficient to form an extended compound;
treating said extended compound with a capping agent;
optionally, treating said extended compound with an oxidizing or sulfurizing agent;
repeating the preceding four steps one or more times to form a further extended compound; and
treating said further extended compound with an oxidizing or sulfurizing agent to form an oligomeric compound.

In certain embodiments, said last treating step cleaves said oligomeric compound from said support medium. Preferably, said last treating step is effective to remove protecting groups present on said oligomeric compound. Preferably, said cleaved oligomeric compound has a terminal hydroxyl group at the site of cleavage and, more preferably, said terminal hydroxyl group is attached to a 2'- or 3'-position of a nucleoside that is located at the 3'-terminus of said oligomeric compound.

In certain other embodiments, the process further comprises the step of treating said oligomeric compound with a reagent effective to cleave said oligomeric compound from said support medium. Preferably, said treating step is effective to remove protecting groups present on said oligomeric compound. Preferably, said cleaved oligomeric compound has a terminal hydroxyl group at the site of cleavage and, more preferably, said terminal hydroxyl group is attached to a 2'- or 3'-position of a nucleoside that is located at the 3'-terminus of said oligomeric compound.

Preferably, the treating step of said reactive hydroxyl group with a monomeric subunit having an activated phosphorus group and a further protected hydroxyl is performed in the presence of an activating agent.

Preferably, said monomeric subunit having an activated phosphorus group is a phosphoramidite, an H-phosphonate and a phosphate triester.

Preferably, said hydroxyl protecting group $Z_1$ and each of said further hydroxyl protecting groups are acid labile.

In certain preferred embodiments of the process, said hydroxyl protecting group $Z_1$ and each of said further hydroxyl protecting groups are removed by contacting said hydroxyl protecting groups with an acid, wherein said acid is formic acid, acetic acid, chloroacetic acid, dichloroacetic acid, trichloroacetic acid, trifluoroacetic acid, benzenesulfonic acid, toluenesulfonic acid, or phenylphosphoric acid.

Preferably, the oligomeric compounds are oligonucleotides, modified oligonucleotides, oligonucleotide analogs, oligonucleosides, oligonucleotide mimetics, hemimers, gapmers or chimeras.

The hydroxyl-protecting group can be removed from the compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See, for example, Greene and Wuts, supra.

The oligomeric compounds prepared in accordance with the process of the invention may be conveniently and routinely made through the well-known technique of support-based synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Preferably, the oligomeric compounds prepared by the process of the invention utilize phosphoramidite chemistry on the support medium. The phosphoramidites can modified at the heterocyclic base, the sugar or both positions to enable the synthesis of fully modified positionally modified oligonucleotides and their analogs.

Conventional iterative solid phase oligonucleotide synthetic regimes are utilized to synthesize the oligomeric compounds of the invention. Representative support-based techniques are those typically employed for DNA and RNA synthesis utilizing standard phosphoramidite chemistry, (see, e.g., *Protocols For Oligonucleotides And Analogs*, Agrawal, S., ed., Humana Press, Totowa, N.J., 1993, hereby incorporated by reference in its entirety). Further details of methods useful for preparing oligonucleotides may be found in Sekine, M., et al., *J. Org. Chem.*, 1979, 44, 2325; Dahl, O., *Sulfur Reports*, 1991, 11, 167–192; Kresse, J., et. al., Nucleic Acids Research, 1975, 2, 1–9; Eckstein, F., *Ann. Rev. Biochem.*, 1985, 54, 367–402; and U.S. Pat. No. 5,210, 264.

A preferred synthetic solid phase synthesis of oligonucleotides utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

The phosphite triester linkage is subsequently oxidized or sulfurized. Choice of oxidizing or sulfurizing agent will determine whether the linkage will be oxidized or sulfurized to a phosphotriester, thiophosphotriester, or a dithiophosphotriester linkage.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, hereby incorporated by reference in its entirety. Treatment with an acid removes the 5'-hydroxyl protecting group, and the synthetic cycle is repeated until the desired oligomer is achieved.

A representative list of capping reagents useful in the process of the present invention include without limitation, acetic anhydride, t-butylphenoxyacetic anhydride, phosphite monoesters, and selected acid chlorides preferably delivered concurrently with a nucleophilic catalyst (e.g. a strong base) such as for example dimethylaminopyridine, N-methylimidazole or triethylamine. Generally capping reagents comprise a mixture of Cap A and Cap B.

Representative mixtures include without limitation:

Cap A: acetic anhydride in acetonitrile or tetrahydrofuran; chloroacetic anhydride in acetonitrile or tetrahydrofuran;

Cap B: N-methylimidazole and pyridine in acetonitrile or tetrahydrofuran; 4-dimethylaminopyridine (DMAP) and pyridine in acetonitrile or tetrahydrofuran; 2,6-lutidine and N-methylimidazole in acetonitrile or tetrahydrofuran.

A more detailed description capping reagents is discussed in U.S. Pat. No. 4,816,571, issued Mar. 28, 1989, which is incorporated herein by reference. A preferred capping reagent is acetic anhydride routinely used as a mixture of cap A and cap B.

Useful sulfurizing agents include Beaucage reagent described in e.g., Iyer et al., *J. Am. Chem. Soc.*, 112, 1253–1254 (1990); and Iyer et al., *J Org Chem*, 55, 4693–4699 (1990); tetraethyl-thiuram disulfide as described in Vu et al., *Tetrahedron Lett.*, 32, 3005–3007 (1991); dibenzoyl tetrasulfide as described in Rao et al., *Tetrahedron Lett.*, 33, 4839–4842 (1992); di(phenylacetyl)disulfide, as described in Kamer, et al., *Tetrahedron Lett.*, 30, 6757–6760 (1989); bis(O,O-diisopropoxy phosphinothioyl)disulfide, Wojciech J. Stec., *Tetrahedron Lett.*, 1993, 34, 5317–5320; sulfur; and sulfur in combination with ligands like triaryl, trialkyl or triaralkyl or trialkaryl phosphines. Useful oxidizing agents, in addition to those set out above, include iodine/tetrahydrofuran/water/pyridine; hydrogen peroxide/water; tert-butyl hydroperoxide; or a peracid like m-chloroperbenzoic acid. In the case of sulfurization, the reaction is performed under anhydrous conditions with the exclusion of air, in particular oxygen; whereas, in the case of oxidation the reaction can be performed under aqueous conditions.

The internucleoside linkages of the oligonucleotides described herein, can be any internucleoside linkage as is known in the art, including phosphorus based linking groups, such as phosphite, phosphodiester, phosphorothioate, and phosphorodithioate linkages. Such linkages can be protected, i.e., they can bear, for example, phosphorus-protecting groups. As used herein, the term "phosphorus protecting group" is intended to denote protecting groups that are known to be useful to protect phosphorus-containing linkages during oligonucleotide synthesis. One such preferred phosphorus-protecting group is the β-cyanoethyl protecting group.

Other representative phosphorus protecting groups include —$CH_2CH=CHCH_2CN$, para-$C_6H_4CH_2CN$, —$(CH_2)_2$-5-N(H)$COCF_3$, —$CH_2CH_2Si(C_6H_5)_2CH_2$, —$CH_2CH_2N(CH_3)COCF_3$ and others known in the art.

The processes of the present invention illustrate the use of activated phosphorus compounds (e.g., compounds having activated phosphorus-containing substituent groups) in coupling reactions. As used herein, the term "activated phosphorus compounds" includes monomers and oligomers that have an activated phosphorus-containing substituent group that is reactive with a hydroxyl group of another monomeric or oligomeric compound to form a phosphorus-containing internucleotide linkage. Such activated phosphorus groups contain activated phosphorus atoms in $P_{III}$ valence state and are known in the art and include, but are not limited to, phosphoramidite, H-phosphonate, phosphate triesters and chiral auxiliaries. A preferred synthetic solid phase synthesis utilizes phosphoramidites as activated phosphates. The phosphoramidites utilize $P_{III}$ chemistry. The intermediate phosphite compounds are subsequently oxidized to the $P^V$ state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

Activated phosphorus groups are useful in the preparation of a wide range of oligomeric compounds including but not limited to oligonucleosides and oligonucleotides as well as oligonucleotides that have been modified or conjugated with other groups at the base or sugar or both. Also included are oligonucleotide mimetics including but not limited to peptide nucleic acids (PNA), morpholino nucleic acids, cyclohexenyl nucleic acids (CeNA), anhydrohexitol nucleic acids, locked nucleic acids (LNA), bicyclic and tricyclic nucleic acids, phosphonomonoester nucleic acids and cyclobutyl nucleic acids. A representative example of one type of oligomer synthesis that utilizes the coupling of an activated phosphorus group with a reactive hydroxyl group is the widely used phosphoramidite approach. A phosphoramidite monomeric subunit is reacted under appropriate conditions with a reactive hydroxyl group to form a phosphite linkage that is further oxidized to a phosphodiester or phosphorothioate linkage. This approach commonly utilizes nucleoside phosphoramidites of the formula:

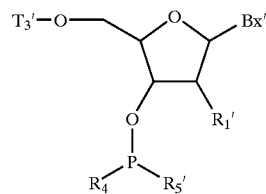

wherein
each Bx' is an optionally protected heterocyclic base moiety;
each $R_{1'}$ is, independently, H or an optionally protected sugar substituent group;

$T_{3'}$ is an hydroxyl protecting group, a nucleoside, a nucleotide, an oligonucleoside or an oligonucleotide;

$R_{4'}$ is $N(L_1)L_2$;

each $L_1$ and $L_2$ is, independently, $C_{1-6}$ alkyl;

or $L_1$ and $L_2$ are joined together to form a 4- to 7-membered heterocyclic ring system including the nitrogen atom to which L1 and L2 are attached, wherein said ring system optionally includes at least one additional heteroatom, wherein said heteroatom is O, N or S;

$R_{5'}$ is $X_1$;

$X_1$ is Pg-O—, Pg-S—, $C_{1-10}$ straight or branched chain alkyl, $CH_3(CH_2)_{0-10}$—O— or —$NR_{6'}R_{7'}$;

Pg is a protecting/blocking group; and each $R_{6'}$ and $R_{7'}$ is, independently, hydrogen, $C_{1-10}$ alkyl, cycloalkyl or aryl;

or optionally, $R_{6'}$ and $R_{7'}$, together with the nitrogen atom to which they are attached form a cyclic moiety that may include an additional heteroatom, wherein said heteroatom is O, S and N; or $R_{4'}$ and $R_{5'}$ together with the phosphorus atom to which $R_{4'}$ and $R_{5'}$ are attached form a chiral auxiliary.

Groups that are attached to the phosphorus atom of internucleotide linkages before and after oxidation ($R_{4'}$ and $R_{5'}$) can include nitrogen containing cyclic moieties such as morpholine. Such oxidized internucleoside linkages include a phosphoromorpholidothioate linkage (Wilk et al., *Nucleosides and Nucleotides*, 1991, 10, 319–322). Further cyclic moieties amenable to the present invention include mono-, bi- or tricyclic ring moieties which may be substituted with groups such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

Some representative examples of $R_{4'}$ and $R_{5'}$ groups that are known to the art skilled and are amenable to the present invention are shown below:

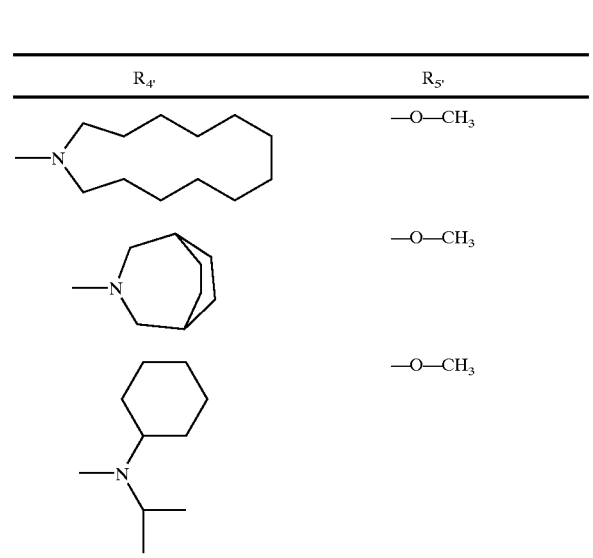

-continued

| R4' | R5' |
|---|---|
| 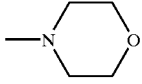 | 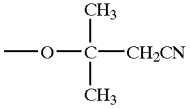 |
| 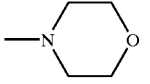 | —O—CH₂CH₂SiCH₃ |
| 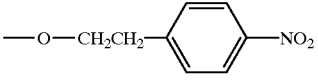 | 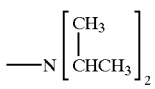 |
| —N(CH₃)₂ | 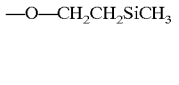 |
| —N(CH₂CH₃)₂ | 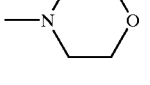 |
| 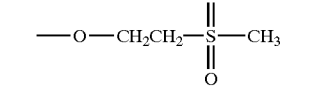 | 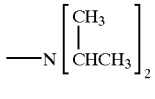 |
| 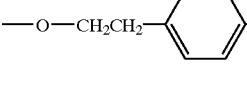 | 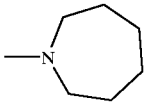 |
| —N(CH₃)₂ | —O—CH₂CCl₃ |
| 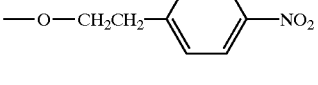 | —CH₂CH=CH₂ |
|  | —O—CH₂CH₂CN |

| R4' | R5' |
|---|---|
| —N(CH₃)₂ | 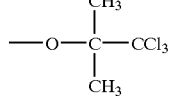 |
| 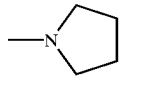 | 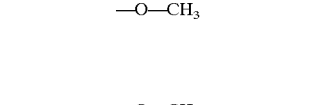 |
|  | 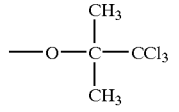 |

-continued

| R4' | R5' |
|---|---|
| 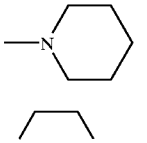 | 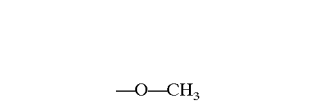 |
| 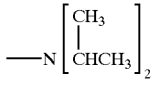 | 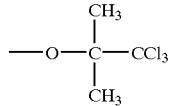 |
| 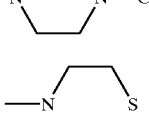 | 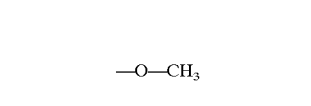 |
| 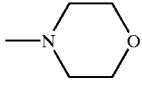 | —O—CH₃ |
| 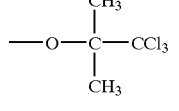 | —O—CH₃ |
| 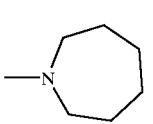 | —O—CH₃ |
| 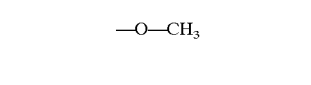 | —O—CH₃ |
|  | —O—CH₃ |
| 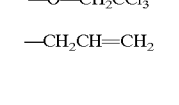 | —O—CH₃ |

Representative nucleobases useful in the methods and conjugated oligomeric compounds of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808, in Chapter 15 by Sanghvi, in *Antisense Research and Application*, Ed. S. T. Crooke and B. Lebleu, CRC Press, 1993, in Englisch et al., *Angewandte Chemie, International Edition*, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607, each of which are hereby incorporated by reference in their entirety. The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2'-sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery*, 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. Pat. No. 6,166,197, hereby incorporated by reference in its entirety.

Sugars having O-substitutions on the ribosyl ring are also amenable to the present invention. Representative substitutions for ring 0 include S, CH$_2$, CHF, and CF$_2$, see, e.g., Secrist, et al., Abstract 21, Program & Abstracts, Tenth International Roundtable, *Nucleosicdes, Nucleotides and their Biological Applications*, Park City, Utah, Sep. 16–20, 1992, hereby incorporated by reference in its entirety.

Representative hydroxyl protecting groups commonly used in the art may be found in Beaucage, et al., *Tetrahedron* 1992, 48, 2223; and Greene and Wuts, *Protective Groups in Organic Synthesis*, Chapter 2, 2d ed, John Wiley & Sons, New York, 1991, each of which are hereby incorporated by reference in their entirety. Preferred protecting groups include dimethoxytrityl (DMT), monomethoxytrityl, 9-phenylxanthen-9-yl (Pixyl) and 9-(p-methoxyphenyl)xanthen-9-yl (Mox). The protecting group can be removed from oligonucleotides of the conjugated oligomeric compound of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See, for example, Greene and Wuts, supra.

In some preferred embodiments of the invention amino groups are appended to alkyl or to other groups such as, for example, to 2'-alkoxy groups. Such amino groups are also commonly present in naturally occurring and non-naturally occurring nucleobases. It is generally preferred that these amino groups be in protected form during the synthesis of oligonucleotides of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Preferably, the process of the invention further comprises the step of treating said oligomeric compound with a reagent effective to cleave said oligomeric compound from said support medium. Preferred cleaving reagents include gaseous ammonia, alkylamines including methylamine, ethylamine, or propylamine, solutions of ammonia, alkylamines including methylamine, ethylamine, propylamine, t-butylamine, piperidine, pyrrolidine, piperazine in water or organic solvents, solutions of alkalis, lithium hydroxide, sodium hydroxide, potassium hydroxide in water or organic solvents including methanol, ethanol, propanol, or isopropanol, solutions of lithium carbonate, sodium carbonate, or potassium carbonate in water or organic solvents including methyl alcohol, or ethyl alcohol.

Preferably, the process further comprises the step of treating said oligomeric compound with a reagent effective to remove protecting groups from said oligomeric compound. Preferred deprotecting reagents include gaseous ammonia, alkylamines including methylamine, ethylamine, or propylamine, solutions of ammonia, alkylamines including methylamine, ethylamine, propylamine, t-butylamine, piperidine, pyrrolidine, piperazine in water or organic solvents, solutions of alkalies lithium hydroxide, sodium hydroxide, potassium hydroxide in water or organic solvents including methanol, ethanol, propanol, or isopropanol, solutions of lithium carbonate, sodium carbonate, or potassium carbonate in water or organic solvents including methyl alcohol, or ethyl alcohol.

Following assembly of the desired oligomeric compound, the next step will normally be deprotection of acid of the oligomeric compound and cleavage of the synthesized oligomeric compound from the support medium. These processes can take place substantially simultaneously, thereby providing the free oligomeric compound in the desired form.

The support media useful with the compounds and in the processes of the invention are used for attachment of a first nucleoside or other monomeric subunit that is then iteratively elongated to give a final oligomeric compound. Support media may be selected to be insoluble or have variable solubility in different solvents to allow the growing support bound polymer to be either in or out of solution as desired. Traditional support media such as solid supports are generally insoluble and are routinely placed in a reaction vessel while reagents and solvents react and or wash the growing chain until cleavage the final polymeric compound. More recent approaches have introduced soluble supports including soluble polymer supports to allow precipitating and dissolving the iteratively synthesized product at desired points in the synthesis (Gravert et al., *Chem. Rev.*, 1997, 97, 489–510).

The current method of choice for the preparation of oligomeric compounds utilizes support media. Support media is used for attachment of a first nucleoside or other monomeric subunit that is then iteratively elongated to give a final oligomeric compound or other polymer such as a polypeptide. Support media can be selected to be insoluble or have variable solubility in different solvents to allow the growing support bound polymer to be either in or out of solution as desired. Traditional support media such as solid supports are for the most part insoluble and are routinely placed in a reaction vessel while reagents and solvents react and or wash the growing chain until cleavage the final polymeric compound. More recent approaches have introduced soluble supports including soluble polymer supports to allow precipitating and dissolving the iteratively synthesized product at desired points in the synthesis (Gravert et al., *Chem. Rev.*, 1997, 97, 489–510).

The term "support media" is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., *Nucleic Acids Research* 1991, 19, 1527); silica-containing particles, such as porous glass beads and silica gel such as that formed by the reaction of trichloro-[3-(4-chloromethyl)phenyl] propylsilane and porous glass beads (see Parr and Grohmann, *Angew. Chem. Internal. Ed.* 1972, 11, 314, sold under the trademark "PORASIL E" by Waters Associates, Framingham, Mass., USA); the mono ester of 1,4-dihydroxymethylbenzene and silica (see Bayer and Jung, *Tetrahedron Lett.*, 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., *Organic Process Research & Development*, 2000, 4, 225–231).

Further support media amenable to the present invention include without limitation PEPS support a polyethylene (PE) film with pendant long-chain polystyrene (PS) grafts (molecular weight on the order of $10^6$, (see Berg, et al., *J. Am. Chem. Soc.*, 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwellplates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113–116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis may be utilized. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175–178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208–210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and U.S. Re. Pat. No. 34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and U.S. Re. Pat. No. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues, A Practical Approach*, Oxford University Press, New York (1991).

In some especially preferred embodiments, the nucleoside components of the oligomeric compounds are connected to each other by optionally protected phosphorothioate internucleoside linkages. Representative protecting groups for phosphorus containing internucleoside linkages such as phosphite, phosphodiester and phosphorothioate linages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and U.S. Re. Pat. No. 34,069 (β-cyanoethyl); Beaucage, S. L. and Iyer, R. P., *Tetrahedron*, 49 No. 10, pp. 1925–1963 (1993); Beaucage, S. L. and Iyer, R. P., *Tetrahedron*, 49 No. 46, pp. 10441–10488 (1993); Beaucage, S. L. and Iyer, R. P., *Tetrahedron*, 48 No. 12, pp. 2223–2311 (1992). Other representative phosphorus protecting groups include —$CH_2CH=CHCH_2CN$, para-$C_6H_4CH_2CN$, —$(CH_2)_2$-5-N(H)$COCF_3$, —$CH_2CH_2Si(C_6H_5)_2CH_2$, —$CH_2CH_2N(CH_3)COCF_3$ and others known in the art.

As used herein, the use in lists in methods or compositions of numbers and letters does not imply any specific sequence or priority, unless explicitly stated.

In a preferred embodiment, the oligomeric compounds produced using the reagents and by the processes of the invention may be administered in an effective amount to an organism to inhibit expression of a gene in the organism. Those skilled in the art would readily be able to determine the effective amount of the oligomeric compound based on the characteristics of the gene.

In another preferred embodiment, the oligomeric compound of the invention may be contacted in an effective amount to kill a pathogenic organism. Those skilled in the art would readily be able to determine the effective amount of the oligomeric compound to kill the organism.

The oligomeric compounds of the invention may be used in the therapeutic and/or prophylactic treatment of unicellular prokaryotic and multicellular eukaryotic organisms that utilize DNA-RNA transcription or RNA-protein transcription as a fundamental part of its hereditary, metabolic or cellular control. Such treatment may include the use of the oligomeric compounds of the invention in a method for killing a pathogenic organism, including viruses, bacteria and eukaryotic parasites.

For therapeutic or prophylactic treatment, the conjugated oligomeric compounds of the invention may be formulated in a pharmaceutical composition, which may include carriers, thickeners, diluents, buffers, preservatives, surface active agents and the like. Pharmaceutical compositions may also include one or more active ingredients such as antimicrobial agents, antiinflammatory agents, anesthetics, and the like in addition to the oligomeric compound of the invention A pharmaceutical composition containing the oligonucleotides and oligonucleotide mimetics produced using the support medium and methods of the invention may be administered in a number of ways depending on whether local or systemic treatment is desired, and on the area to be treated. Administration may be performed topically (including ophthalmically, vaginally, rectally, transdermally, intranasally), orally, by inhalation, or parenterally, for example by intravenous infusion, drip or injection, or subcutaneous, intraperitoneal or intramuscular injection.

In addition, the oligonucleotides and oligonucleotide mimetics produced using the support medium and methods of the invention may be used for diagnostic and research purposes, as will be apparent to those skilled in the art.

Compounds containing the oligonucleotides and oligonucleotide mimetics produced using the support medium and methods of the invention are preferably specifically hydridizable with a target region. By "specifically hybridizable" herein is meant capable of forming a stable duplex with a target DNA or RNA. It is believed that oligonucleotides that form Watson-Crick base pairs, i.e. are complementary with target DNA or RNA and which specifically hybridize with target DNA or RNA inhibit the flow of genetic information from DNA to protein. In some embodiments of the present invention the oligonucleotide portions of compounds of the present invention are at least 70% complementary to a target sequence. In preferred embodiments of the present invention the oligonucleotide portions of compounds of the present invention are at least 80% complementary to a target sequence. 100% complementarity of the oligonucleotide portions of compounds of the present invention to a target sequence is most preferred. In preferred embodiments of the present invention, the oligonucleotide portions may be specifically hybridizable with DNA or RNA from papilloma virus, herpes viruses, human immunodeficiency virus, Candida, cytomegaloviruses, and influenza viruses. In addition, the oligonucleotide portions may also be specifically hybridizable with endogenous DNA or RNA of a cell.

For therapeutics, an animal suspected of having a disease characterized by excessive or abnormal production of a protein is treated by administering the oligomeric compounds of the invention in a pharmaceutically acceptable carrier. Most preferable, the compound is hybridizable with an RNA coding for the protein. Persons of ordinary skill in the art can easily determine optimum dosages, dosing methodologies and repetition rates. Such treatment is generally continued until either a cure is effected or a diminution in the diseased state is achieved. Long term treatment is likely for some diseases.

The oligonucleotides and oligonucleotide mimetics produced using the support medium and methods of the invention will also be useful as a research reagent useful for the modulation of the production of a protein by an organism. Modulation may be accomplished by contacting the organism with the conjugated oligomeric compounds of the invention. Preferably the compounds are hybridizable with RNA coding for the protein.

Diagnostic applications include the detection of the presence or absence of an RNA in a sample suspected of containing RNA comprising contacting the sample with a conjugated oligomeric compound of the present invention wherein the conjugated oligomeric compound is specifically hybridizable with the RNA and detecting the presence or absence of hybridization of the compound to the sample wherein hybridization is indicative of the present of the RNA in the sample.

The oligonucleotides and oligonucleotide mimetics produced using the support medium and methods of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The oligonucleotides and oligonucleotide mimetics produced using the support medium and methods of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2- thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2-or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The oligonucleotides and oligonucleotide mimetics produced using the support medium and methods of the invention can be utilized for diagnostics, therapeutics, prophylaxis and as research reagents and kits. For therapeutics, an animal, preferably a human, suspected of having a disease or disorder that can be treated by modulating the expression of a particular target gene is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The oligonucleotides and oligonucleotide mimetics produced using the support medium and methods of the invention are useful for research and diagnostics, because these compounds can be prepared to hybridize to nucleic acids encoding a particular protein, enabling sandwich and other assays to easily be constructed to exploit this fact. Hybridization of the antisense oligonucleotides of the invention with a nucleic acid encoding a particular protein can be detected by means known in the art. Such means may include conjugation of an enzyme to the oligonucleotide, radiolabelling of the oligonucleotide or any other suitable detection means. Kits using such detection means for detecting protein levels in a sample may also be prepared.

The present invention also includes pharmaceutical compositions and formulations that include the oligonucleotides and oligonucleotide mimetics produced using the support medium and methods of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof). Topical formulations are described in detail in United States patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydrofusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyomithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999), each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions containing the oligonucleotides and oligonucleotide mimetics produced using the support medium and methods of the invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations containing the oligonucleotides and oligonucleotide mimetics produced using the support medium and methods of the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The containing the oligonucleotides and oligonucleotide mimetics produced using the support medium and methods of the invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The compositions containing the oligonucleotides and oligonucleotide mimetics produced using the support medium and methods of the invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug that may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., Volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture has been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the oligonucleotides and oligonucleotide mimetics produced using the support medium and methods of the invention are formulated as microemulsions. A microemulsion may be defined as a system of water, oil and amphiphile that is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions containing the oligonucleotides and oligonucleotide mimetics produced using the support medium and methods of the invention of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome that is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage*

*Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes that are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesteroupolyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term that, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993,53, 3765). Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (*FEBS Lett.*, 990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets that are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

As used herein, "non-chelating non-surfactant penetration enhancing compounds" can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrolazones, and terpenes such as limonene and menthone.

Certain compositions of the present invention containing the oligonucleotides and oligonucleotide mimetics produced using the support medium and methods of the invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration that do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration that do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions containing the oligonucleotides and oligonucleotide mimetics produced using the support medium and methods of the invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances that increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The following examples are illustrative but are not meant to be limiting of the present invention.

EXAMPLES

Example 1

(1α,2α,3α,4α,5α,6α)-5,6-Dihydroxy-7-oxabicyclo[2.2.1]heptane-2,3-dicarboxylic Acid (2)

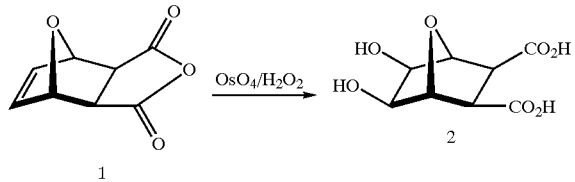

A solution of commercial (3aR,4S,7R,7aS)-rel-3a,4,7,7a-tetrahydro-4,7-epoxyisobenzofuran-1,3-dione, 1, (9.05 g, 54.5 mmol) in hydrogen peroxide (30% aqueous, 2.97 g, 87.2 mmol), acetone (72.5 mL), ether (18.1 mL), and t-butanol (6.2 mL) was treated with osmium tetroxide (56 mg, 0.22 mmol) in t-butanol (2.86 mL) for 4 days at 28–30° C. The reaction mixture was treated with ether (90 mL) and kept at 4° C. for 1 h. The precipitate was filtered off, washed with ether and dried to give pure 2 (8.08 g, 68.0%). The compound may be re-crystallized from ethanol.

Example 2
(1α,2α,3α,4α,5α,6α)-5-Hydroxy-6-(4,4'-dimethoxytrityloxy)-7-oxabicyclo[2.2.1]heptane-2,3-dicarboxylic Acid (3)

4,4'-Dimethoxytrityl chloride (7.75 g, 22.9 mmol) was added in four portions to a

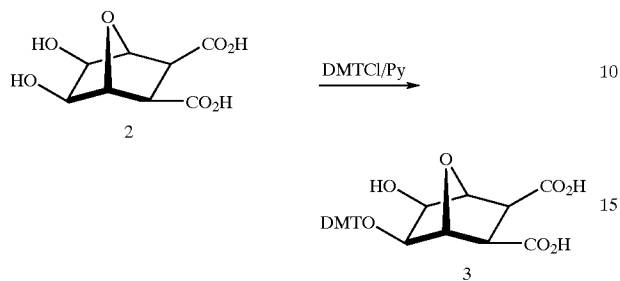

solution of compound 2 (3.39 g, 15.5 mmol) in pyridine (50 mL) over a period of 2 days. The solvent was evaporated, and the residue was treated with ethyl acetate (200 mL) and 1 M aqueous triethylammonium acetate (20 mL). The organic solution was washed with 1 M aqueous triethylammonium acetate (20 mL), treated with MeOH (20 mL), dried over $Na_2SO_4$, and evaporated. The residue was dissolved in ethyl acetate (50 mL) and treated with ether (50 mL). A crystalline precipitate was collected, washed with ether, and dried to give 3 (6.28 g, 65%).

Example 3
(1α,2α,3α,4α,5α,6α)-5-(Acetoxy)-6-(4,4'-dimethoxytrityloxy)-7-oxabicyclo[2.2.1]heptane-2,3-dicarbanhydride (4)

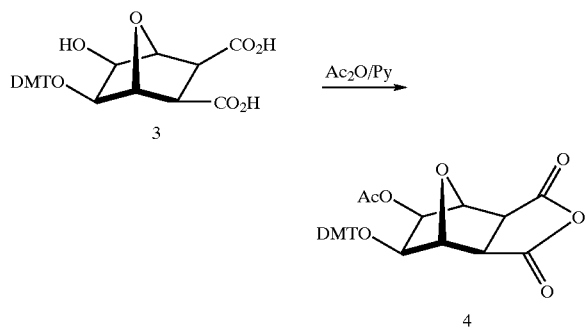

Compound 3 (1.57 g, 3.0 mmol) was treated with acetic anhydride (3.0 g) and pyridine (15 mL) for 3 h at room temperature. The mixture was evaporated and co-evaporated with pyridine (5×15 mL) to give the title compound as a colorless foam, which was used in the next step without any further purification.

Example 4
Support Medium 5

Aminoalkyl controlled pore glass (4.0 g, 0.51 mmol) was gently shaken with compound 4 (2.65 mmol) in pyridine (17 mL) overnight. The suspension was filtered, and the solid support was washed with pyridine (3×20 mL). The collected solution was evaporated, the residue was, upon treatment with acetic anhydride as described above, stored for loading another portion of aminoalkyl CPG. The solid support was additionally washed with ethyl acetate, dried, and capped by treating with a mixture of $Ac_2O$/pyridine/N-methylimidazole/THF (10:10:10:70) for 3 h at room temperature. Finally, the solid support 5 was washed with MeCN and ethyl acetate and dried. The loading of 5 (57±0.4 μmol $g^{-1}$) was determined by the standard DMT assay.

Example 5
Support Medium 6.

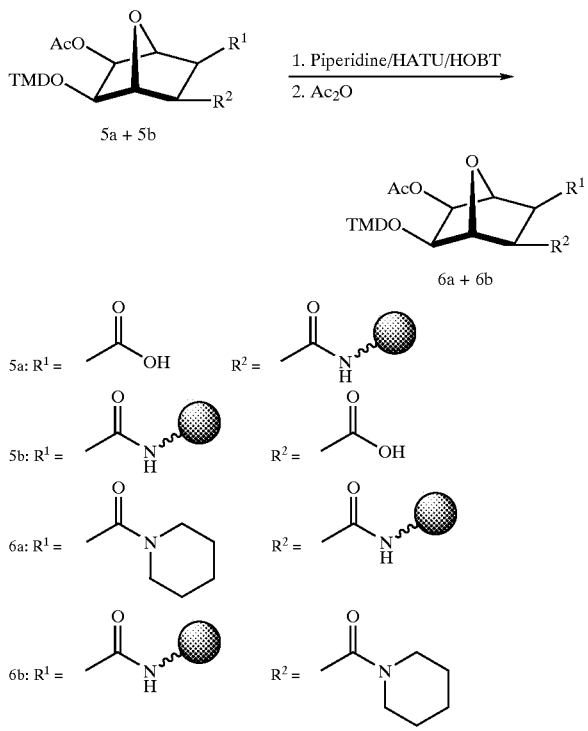

The solid support 5 (1.0 g) was treated with 0.4 M HATU and 0.3 M HOBT in MeCN-pyridine (4:1, 6 mL) for 5 minutes. The liquid phase was removed, and the solid support was treated with 0.5 M piperidine in MeCN (5 mL) for 15 minutes. The solid support was washed with MeCN (5×10 mL) and capped with a mixture of $Ac_2O$/pyridine/N-methylimidazole/THF (10:10:10:70) for 3 hours at room temperature. Finally, the solid support 5 was washed with MeCN and ethyl acetate and dried. The loading of 5 (57±0.4 μmol $g^{-1}$) was determined by the standard DMT assay.

Example 6
Support Medium 7.

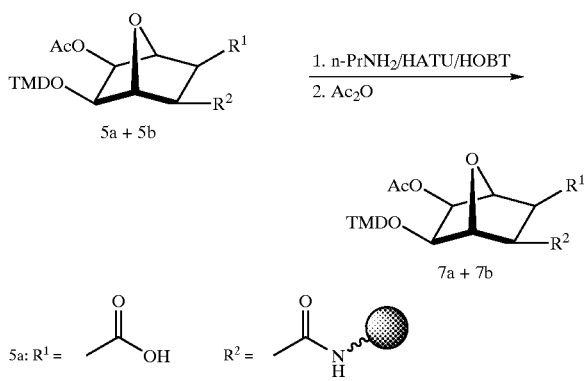

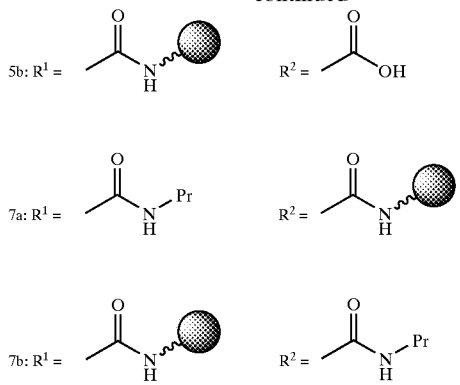
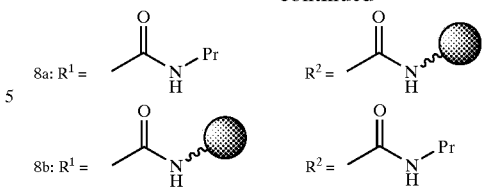

The solid support 5 (1.0 g) was treated with 0.4 M HATU and 0.3 M HOBT in MeCN-pyridine (4:1, 6 mL) for 5 minutes. The liquid phase was removed, and the solid support was treated with 0.5 M n-propylamine in MeCN (5 mL) for 15 minutes. The solid support was washed with MeCN (5×10 mL) and capped with a mixture of Ac$_2$O/pyridine/N-methylimidazole/THF (10:10:10:70) for 3 hours at room temperature. Finally, the solid support 5 was washed with MeCN and ethyl acetate and dried. The loading of 5 (57±0.4 μmol g$^{-1}$) was determined by the standard DMT assay.

Example 7

Support Medium 8.

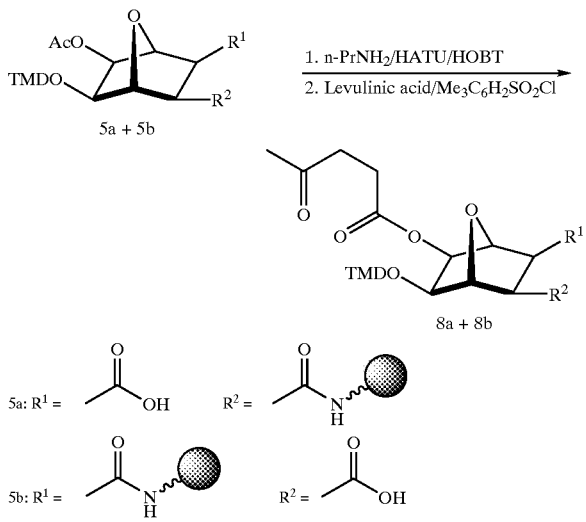

The solid support 5 (1.0 g) is treated with 0.4 M HATU and 0.3 M HOBT in MeCN-pyridine (4:1, 6 mL) for 5 minutes. The liquid phase is removed, and the solid support is treated with 0.5 M n-propylamine in MeCN (2×5 mL) for 15 and 90 minutes. The solid support is washed with MeCN (5×10 mL) and capped with a mixture of 0.5 M levulinic acid, 0.5 M mesitylene sulfonyl chloride, 0.5 M N-methylimidazole, and 1.5 M ethyldiisopropylamine in pyridine/THF (25:75) for 6 hours at room temperature. Finally, the solid support 8 is washed with MeCN and ethyl acetate and dried. The loading of 8 (57±0.4 μmol g$^{-1}$) was determined by the standard DMT assay.

Example 8

Synthesis of Oligonucleotides on Support Media 5–7

The oligonucleotide synthesis was performed on an ABI 380B DNA Synthesizer on a 1 to 4 μmol scale according to the manufacturer's recommendations. The standard and 2'-O-(2-methoxyethyl)phosphoramidites were used as 0.1 M solutions in anhydrous MeCN. The oxidation step was carried out with the standard iodine reagent or with t-butyl hydroperoxide (10% in MeCN) for 10 minutes. The preparation of oligonucleotide phosphorothioates was carried out using 3H-1,2-benzodithiol-3-one 1,1-dioxide (0.05 M in MeCN) as a sulfur-transfer reagent. Optionally, oligonucleotide phosphorothioates were synthesized using oxidation with the standard iodine reagent or t-butyl hydroperoxide solution for the linkage between the solid support and the 3'-terminal nucleoside while the internucleosidic linkages were sulfurized in a conventional manner.

The detritylation time for the solid supports 5 and 6 was extended to 6 minutes while the solid support 7 was detritylated according to the standard protocol. The coupling time of minutes was used for 2'-O-(2-methoxyethyl) phosphoramidites and for the attachment of the 3'-terminal nucleoside residues to universal solid supports 5–7.

Example 9

Analysis of Product Distribution in Oligonucleotides Synthesized on Support Media 5–7

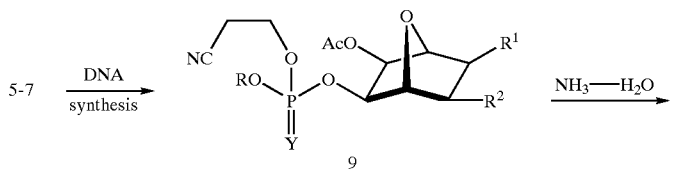

9

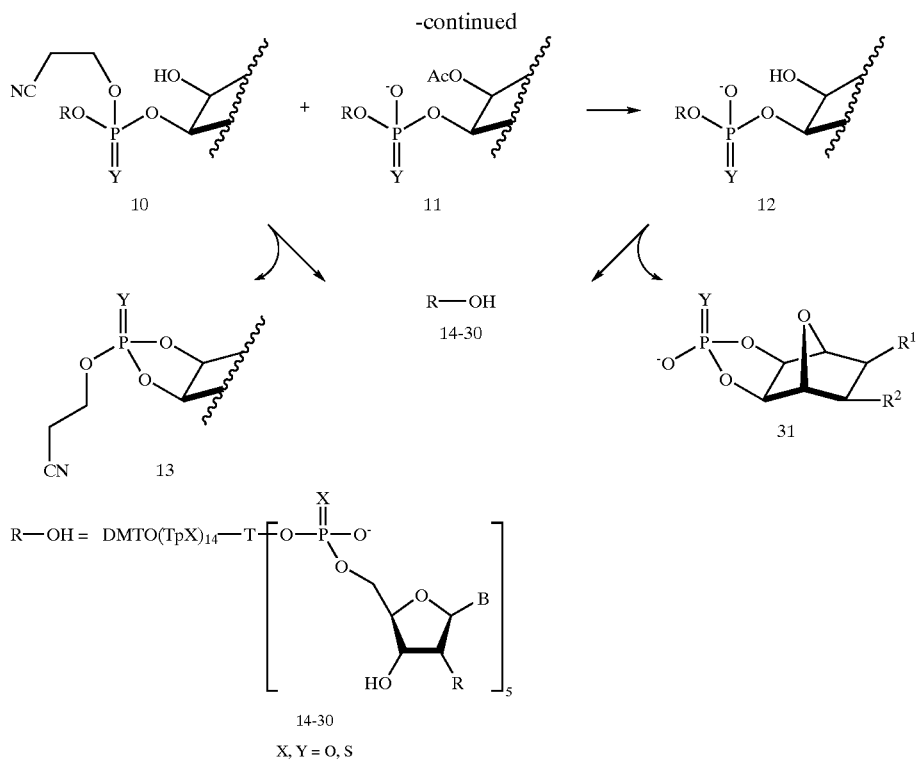

The solid support-bound oligonucleotides 9 were deprotected with concentrated aqueous ammonium hydroxide under the standard conditions (8 h at 55° C.). The liquid phase was withdrawn and evaporated to give crude oligonucleotides 14–30 specified in Table 1. Spectrophotometric determination at 260 nm demonstrated the crude yields being in the expected range of 70 to 100 OD $\mu\text{mol}^{-1}$ (Table 2). The 5'-DMT protected oligonucleotides were analyzed by reverse phase HPLC on a DeltaPak C18 column (Waters, 3.8×300 mm) using a linear gradient from 0 to 50% MeCN in 0.1 M ammonium acetate. The crude products were further characterized by ES MS to show no side products bearing a 3'-derivatized hydroxy group.

Example 10
Experimental Setup for Recording the Kinetics of Chemical Reactions on Solid Surfaces in Continuous Flow An apparatus comprising a liquid metering pump, thermostat, reagent loop, switching valve, reaction vessel, and data acquisition system was assembled. A reagent was continuously delivered to the reagent loop where it was brought to a desired temperature. On leaving the loop, the reagent contacted a solid phase placed in the thermostated plug-flow reactor. The products dissolved in the reagent were eluted to a detector chosen in accordance with the nature of compounds whose concentration was to be measured. The data were acquired and stored by an attached computer system. Optionally, fractions of the reagent containing dissolved products were collected and re-analyzed off-line by a different method, for instance, HPLC.

Example 11
Determination of the Time Required for the 95% Release of Oligonucleotides Synthesized on 5–7

A solid-support-bound oligonucleotide 9 (0.1 to 1 $\mu$mol) was placed in the reaction vessel thermostated at 27.05° C. for 30 minutes. The data collection was started, and aqeous ammonium hydroxide (14.3 M, 27.1%) was delivered to the reaction vessel for 7 to 10 hours at a constant flow of 0.5 mL $\text{min}^{-1}$. The recorded data were integrated and deconvoluted to determine the time required for the 95% release of oligonucleotides 14–30 from the universal solid support 7 (Table 1). The oligonucleotide 17 synthesized on solid support 5 and 6 was released at a rate equal to that for the solid support 7.

TABLE 1

| Oligonucleotide | | | | | 95% release |
|---|---|---|---|---|---|
| Compound | Base | R | X | Y | (minutes) |
| 14 | A | H | O | O | 238 |
| 15 | G | H | O | O | 272 |
| 16 | C | H | O | O | 251 |
| 17 | T | H | O | O | 256 |
| 15 | A | H | S | S | 343 |
| 19 | G | H | S | S | 456 |
| 20 | G | H | S | O | 280 |
| 21 | C | H | S | S | 365 |
| 22 | T | H | S | S | 382 |
| 23 | G | MOE | O | O | 180 |
| 24 | 5-Me-U | MOE | O | O | 129 |
| 25 | A | MOE | S | S | 161 |
| 26 | G | MOE | S | S | 212 |
| 27 | G | MOE | S | O | 185 |
| 28 | 5-Me-C | MOE | S | S | 159 |
| 29 | 5-Me-U | MOE | S | S | 182 |
| 30 | U | Ome | O | O | 123 |

Abbreviations:
A = adenine, G = guanine, C = cytosine, T = thymine
5-Me-C = 5-methyl-cytosine; 5-Me-U = 5-methyl uracil
MOE = methoxyethoxy
OMe = methoxy
H = hydrogen; O = oxygen; S = sulfur

TABLE 2

| Compound | Base | R | X | Y | Crude Yield, OD $\mu mol^{-1}$ |
|---|---|---|---|---|---|
| 14 | A | H | O | O | 84 |
| 15 | G | H | O | O | 82 |
| 16 | C | H | O | O | 101 |
| 17 | T | H | O | O | 94 |
| 25 | A | MOE | S | S | 72 |
| 26 | G | MOE | S | S | 87 |
| 27 | 5-Me-C | MOE | S | S | 110 |
| 28 | 5-Me-U | MOE | S | S | 110 |

Example 12

Universal Solid Support 31

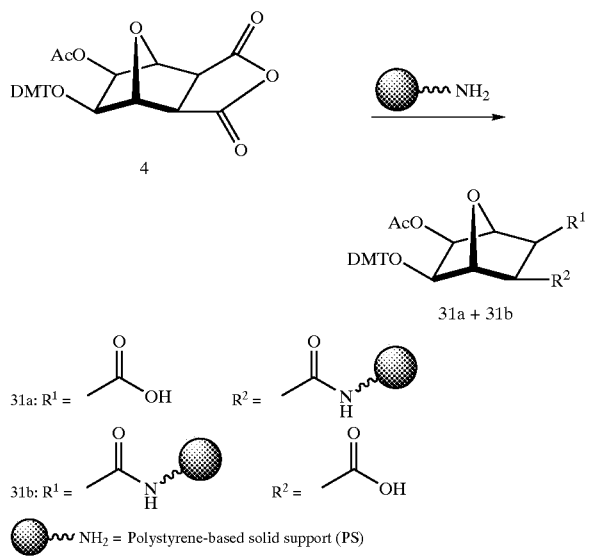

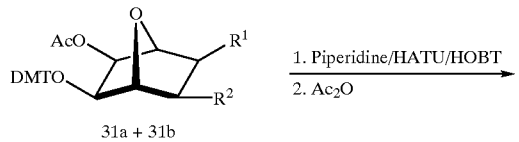

A polystyrene-based solid support Primer 30 HL (13.5 g, 2.7 mmol) was gently shaken with compound 4 (0.73 g, 1.34 mmol) in pyridine (150 mL) overnight. The suspension was filtered, and the solid support was washed with pyridine (3×100 mL). The solid support was additionally washed with ethyl acetate, dried, and capped by treating with a mixture of Ac$_2$O/pyridine/N-methylimidazole/THF (10:10:10:70) for 3 hours at room temperature. Finally, the solid support 31 was washed with MeCN and ethyl acetate and dried. The loading of 31 (96 $\mu$mol g$^{-1}$) was determined by the standard DMT assay.

Example 13

Universal Solid Support 32

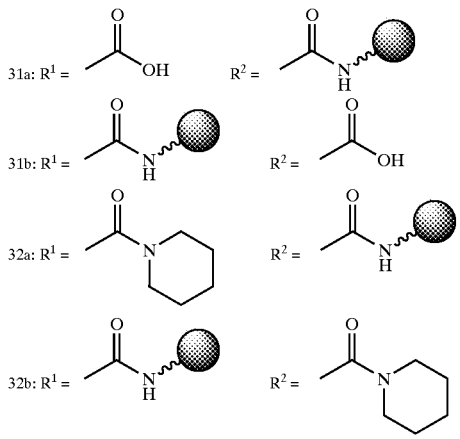

The solid support 31 (1.0 g) was treated with 0.2 M HATU and 0.23 M HOBT in MeCN-pyridine (4:1, 10 mL) for 5 minutes. The liquid phase was removed, and the solid support was treated with 0.5 M piperidine in MeCN (10 mL) for 15 minutes. The solid support was washed with MeCN (5×10 mL) and capped with a mixture of Ac$_2$O/pyridine/N-methylimidazole/THF (10:10:10:70) for 3 hours at room temperature. Finally, the solid support 32 was washed with MeCN and ethyl acetate and dried. The loading of 32 (96 $\mu$mol g$^{-1}$) was determined by the standard DMT assay.

Example 14

Universal Solid Support 33

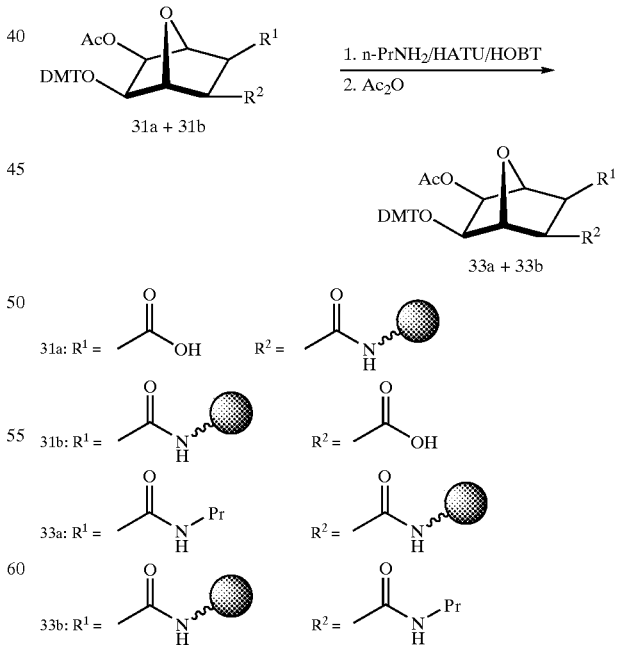

The solid support 31 (10.0 g) was treated with 0.2 M HATU and 0.2 M HOBT in MeCN-pyridine (4:1, 80 mL) for 5 minutes. The liquid phase was removed, and the solid support was treated with 0.5 M n-propylamine in MeCN (100 mL) for 15 minutes. The solid support was washed with MeCN (5×100 mL) and capped with a mixture of Ac$_2$O/pyridine/N-methylimidazole/THF (10:10:10:70) for 3 h at room temperature. Finally, the solid support 33 was washed with MeCN and ethyl acetate and dried. The loading of 33 (96 μmol g$^{-1}$) was determined by the standard DMT assay.

Example 15
Universal Solid Support 34

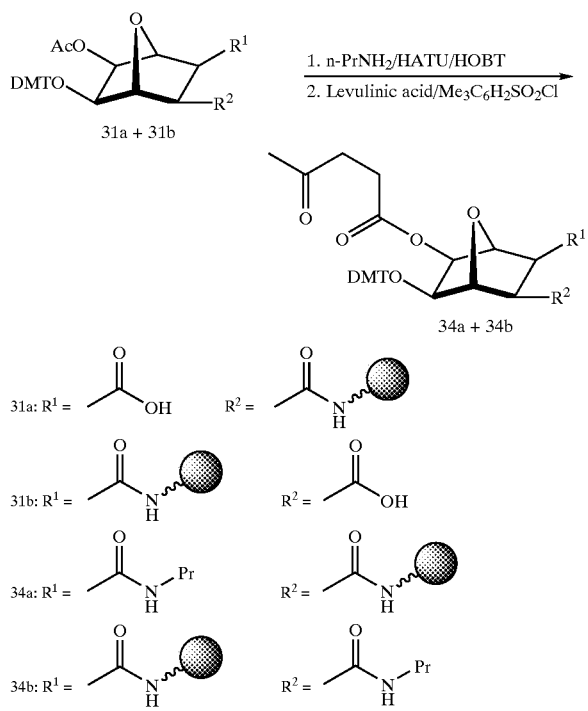

The solid support 31 (1.0 g) is treated with 0.2 M HATU and 0.2 M HOBT in MeCN-pyridine (4:1, 10 mL) for 5 minutes. The liquid phase is removed, and the solid support is treated with 0.5 M n-propylamine in MeCN (2×5 mL) for 15 and 90 minutes. The solid support is washed with MeCN (5×10 mL) and capped with a mixture of 0.5 M levulinic acid, 0.5 M mesitylene sulfonyl chloride, 0.5 M N-methylimidazole, and 1.5 M ethyldiisopropylamine in pyridine/THF (25:75) for 6 h at room temperature. Finally, the solid support 34 is washed with MeCN and ethyl acetate and dried. The loading of 34 (96 μmol g$^{-1}$) is determined by the standard DMT assay.

Example 16
Universal Solid Support 35

An aminopolystyrene PS 200 (10 g, 2 mmol) was gently shaken with compound 4 (0.73 g, 1.34 mmol) in pyridine (150 mL) overnight. The suspension was filtered, and the solid support was washed with pyridine (3×100 mL). The solid support was additionally washed with ethyl acetate, dried, and capped by treating with a mixture of Ac$_2$O/pyridine/N-methylimidazole/THF (10:10:10:70) for 3 h at room temperature. Finally, the solid support 35 was washed with MeCN and ethyl acetate and dried. The loading of 35 (ca 100 μmol g$^{-1}$) was determined by the standard DMT assay.

Example 17
Universal Solid Support 36

The solid support 35 (10.0 g) was treated with 0.2 M HATU and 0.2 M HOBT in MeCN-pyridine (4:1, 80 mL) for 5 minutes. The liquid phase was removed, and the solid support was treated with 0.5 M n-propylamine in MeCN (100 mL) for 15 minutes. The solid support was washed with MeCN (5×100 mL) and capped with a mixture of Ac$_2$O/pyridine/N-methylimidazole/THF (10:10:10:70) for 3 hours at room temperature. Finally, the solid support 36 was washed with MeCN and ethyl acetate and dried. The loading of 36 (ca. 100 μmol g$^{-1}$) was determined by the standard DMT assay.

Example 18
Universal Solid Support 37

A Merckogel solid support (2 mmol) was gently shaken with compound 4 (0.73 g, 1.34 mmol) in pyridine (150 mL) overnight. The suspension was filtered, and the solid support was washed with pyridine (3×100 mL). The solid support was additionally washed with ethyl acetate, dried, and capped by treating with a mixture of Ac$_2$O/pyridine/N-methylimidazole/THF (10:10:10:70) for 3 hours at room temperature. Finally, the solid support 37 was washed with MeCN and ethyl acetate and dried. The loading of 37 (ca 100 μmol g$^{-1}$) was determined by the standard DMT assay.

Example 19
Universal Solid Support 38

The solid support 37 (10.0 g) was treated with 0.2 M HATU and 0.2 M HOBT in MeCN-pyridine (4:1, 80 mL) for 5 minutes. The liquid phase was removed, and the solid support was treated with 0.5 M n-propylamine in MeCN (100 mL) for 15 minutes. The solid support was washed with MeCN (5×100 mL) and capped with a mixture of Ac$_2$O/pyridine/N-methylimidazole/THF (10:10:10:70) for 3 hours at room temperature. Finally, the solid support 38 was washed with MeCN and ethyl acetate and dried. The loading of 38 (ca. 100 μmol g$^{-1}$) was determined by the standard DMT assay.

Example 20
Universal Solid Support 39

A Tentagel solid support (2 mmol) was gently shaken with compound 4 (0.73 g, 1.34 mmol) in pyridine (150 mL) overnight. The suspension was filtered, and the solid support was washed with pyridine (3×100 mL). The solid support was additionally washed with ethyl acetate, dried, and capped by treating with a mixture of Ac$_2$O/pyridine/N-methylimidazole/THF (10:10:10:70) for 3 hours at room temperature. Finally, the solid support 39 was washed with MeCN and ethyl acetate and dried. The loading of 39 (ca 100 μmol g$^{-1}$) was determined by the standard DMT assay.

Example 21
Universal Solid Support 40

The solid support 39 (10.0 g) was treated with 0.2 M HATU and 0.2 M HOBT in MeCN-pyridine (4:1, 80 mL) for 5 minutes. The liquid phase was removed, and the solid support was treated with 0.5 M n-propylamine in MeCN (100 mL) for 15 minutes. The solid support was washed with MeCN (5×100 mL) and capped with a mixture of Ac$_2$O/pyridine/N-methylimidazole/THF (10:10:10:70) for 3 hours at room temperature. Finally, the solid support 40 was washed with MeCN and ethyl acetate and dried. The loading of 40 (ca. 100 μmol g$^{-1}$) was determined by the standard DMT assay.

Example 22
Utilization of —OH Containing Supports

The hydroxyl containing support is treated with CDI followed by 1,6-diaminohexane. This provides amine-containing supports.

Example 23
Carbamate Linked Supports

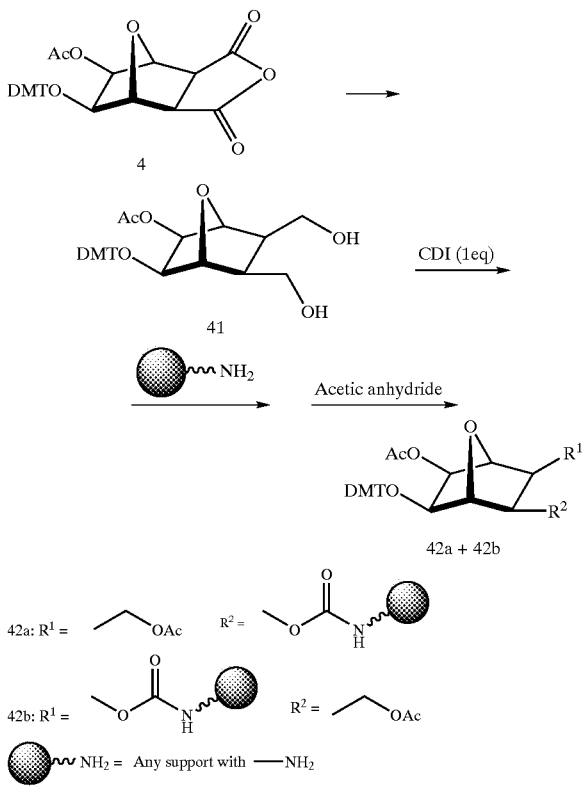

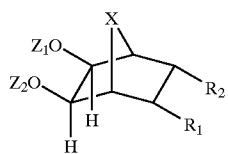

$\sim$NH$_2$ = Any support with —NH$_2$

Compound 4 is reduced to the diol compound 41 using LiAlH$_4$. It is treated with 1 equivalent of CDI followed by the reaction support followed by capping with acetic anhydride. This results in carbamate containing reaction supports.

What is claimed:

1. A compound of Formula I:

I wherein:
X is CH$_2$, O, S or NR$_3$;
R$_3$ is alkyl, —C(=O)alkyl or an amino protecting group;
one of R$_1$ and R$_2$ is —(L)$_n$-sm and the other of R$_1$ and R$_2$ is —C(=O)—R$_4$ or —C(=S)—R$_4$;
L is a linking moiety;
n is 0 or 1;
sm is a support medium;
R$_4$ is —O-alkyl, —N(J$_1$)J$_2$;
  J$_1$ is H or alkyl;
  J$_2$ is alkyl or a nitrogen-protecting group;
  or J$_1$ and J$_2$ together with the nitrogen atom to which they are attached form a ring structure; and
Z$_1$ and Z$_2$ are orthogonal hydroxyl protecting groups.

2. The compound of claim 1, wherein X is O, S or NR$_3$.

3. The compound of claim 2, wherein R$_3$ is alkyl or —C(=O)alkyl.

4. The compound of claim 1, wherein:
X is O; and
one of R$_1$ and R$_2$ is —(L)$_n$-sm and the other of R$_1$ and R$_2$ is —C(=O)—R$_4$.

5. The compound of claim 4, wherein L is —C(=O)—.

6. The compound of claim 4, wherein R$_4$ is —N(H)alkyl or N-piperidinyl.

7. The compound of claim 4, wherein Z$_1$ is —C(=O)CH$_3$ and Z$_2$ is dimethoxytrityl.

8. The composition of claim 1, wherein said support medium is a controlled pore glass, oxalyl-controlled pore glass, silica-containing particles, polymers of polystyrene, copolymers of polystyrene, copolymers of styrene and divinylbenzene, copolymers of dimethylacrylamide and N,N'-bisacryloylethylenediamine, soluble support medium, or PEPS.

9. The compound of claim 8, wherein said support medium is controlled pore glass, polymers of polystyrene or copolymers of polystyrene.

10. The compound of claim 1, wherein Z$_1$ is trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, 9-fluorenylmethoxycarbonyl, levulinyl or acetoacetyl groups.

11. The compound of claim 1, wherein Z$_2$ is 4,4'-dimethoxytrityl, monomethoxytrityl, 9-phenylxanthen-9-yl, 9-(p-methoxyphenyl)xanthen-9-yl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetyl, chloroacetyl, trichloroacetyl, trifluoroacetyl, pivaloyl, benzoyl, p-phenylbenzoyl, mesyl, tosyl, 4,4',4"-tris-(benzyloxy)trityl, 4,4',4"-tris-(4,5-dichlorophthalimido)trityl, 4,4',4"-tris(levulinyloxy)trityl, 3-(imidazolylmethyl)-4,4'-dimethoxytrityl, 4-decyloxytrityl, 4-hexadecyloxytrityl, 9-(4-octadecyloxyphenyl)xanthene-9-yl, 1,1-bis-(4-methoxyphenyl)-1'-pyrenyl methyl, p-phenylazophenyloxycarbonyl, 9-fluorenylmethoxycarbonyl, 2,4-dinitrophenylethoxycarbonyl, 4-(methylthiomethoxy)butyryl, 2-(methylthiomethoxymethyl)benzoyl, 2-(isopropylthiomethoxymethyl)benzoyl, 2-(2,4-dinitrobenzenesulphenyloxymethyl)benzoyl, or levulinyl groups.

12. A method for functionalizing a support medium with a first monomeric subunit, comprising:
providing a support bound compound of Formula I:

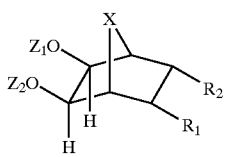

wherein
X is $CH_2$, O, S or $NR_3$;
$R_3$ is alkyl, —C(=O)alkyl or an amino protecting group;
one of $R_1$ and $R_2$ is —(L)$_n$-sm and the other of $R_1$ and $R_2$ is —C(=O)—$R_4$ or —C(=S)—$R_4$;
L is a linking moiety;
n is 0 or 1;
sm is a support medium;
$R_4$ is —O-alkyl, —N($J_1$)$J_2$;
$J_1$ is H or alkyl;
$J_2$ is alkyl or a nitrogen-protecting group;
or $J_1$ and $J_2$ together with the nitrogen atom to which they are attached form a ring structure; and
$Z_1$ and $Z_2$ are orthogonal hydroxyl protecting groups;
selectively deblocking one of said orthogonal hydroxyl protecting groups to give a reactive hydroxyl group; and
treating said reactive hydroxyl group with a first monomeric subunit having an activated phosphorus group and a further protected hydroxyl group thereon for a time and under conditions sufficient to form a monomer-functionalized support medium.

13. The method of claim 12, further comprising:
treating said monomer-functionalized support medium with a capping agent; and
optionally, treating said monomer-functionalized support medium with an oxidizing agent.

14. The method of claim 13 further comprising:
deblocking said further protected hydroxyl group to give a reactive hydroxyl group;
treating said reactive hydroxyl group with a further monomeric subunit having an activated phosphorus group and a further protected hydroxyl group thereon for a time and under conditions sufficient to form an extended compound;
treating said extended compound with a capping agent;
optionally, treating said extended compound with an oxidizing or sulfurizing agent;
repeating the preceding four steps one or more times to form a further extended compound; and
treating said further extended compound with an oxidizing or sulfurizing agent to form an oligomeric compound.

15. The process of claim 14, wherein treating said further extended compound with said oxidizing or sulfurizing agent to form said oligomeric compound cleaves said oligomeric compound from said support medium.

16. The process of claim 14, wherein treating said further extended compound with said oxidizing agent to form said oligomeric compound removes protecting groups present on said oligomeric compound.

17. The process of claim 15, wherein said cleaved oligomeric compound has a terminal hydroxyl group at the site of cleavage.

18. The process of claim 17, wherein said terminal hydroxyl group is attached to a 2'- or 3'-position of a nucleoside that is located at the 3'-terminus of said oligomeric compound.

19. The process of claim 14, further comprising a step of treating said oligomeric compound with a reagent effective to cleave said oligomeric compound from said support medium.

20. The process of claim 19, wherein said treating said oligomeric compound with a reagent effective to cleave said oligomeric compound removes protecting groups present on said oligomeric compound.

21. The process of claim 19, wherein said cleaved oligomeric compound has a terminal hydroxyl group at the site of cleavage.

22. The process of claim 21, wherein said terminal hydroxyl group is attached to a 2'- or 3'-position of a nucleoside that is located at the 3'-terminus of said oligomeric compound.

23. The process of claim 14, wherein said treating of said reactive hydroxyl group with a further monomeric subunit is performed in the presence of an activating agent.

24. The process of claim 12, wherein X is O, S or $NR_3$.

25. The process of claim 12, wherein $R_3$ is alkyl or —C(=O)alkyl.

26. The process of claim 12, wherein X is O and one of $R_1$ and $R_2$ is —(L)$_n$-sm and the other of $R_1$ and $R_2$ is —C(=O)—$R_4$.

27. The process of claim 26, wherein L is —C(=O)—.

28. The process of claim 26, wherein $R_4$ is —N(H)alkyl or N-piperidinyl.

29. The process of claim 26, wherein $Z_1$ is —C(=O)$CH_3$; and $Z_2$ is dimethoxytrityl.

30. The process of claim 12, wherein said support medium is controlled pore glass, oxalyl-controlled pore glass, silica-containing particles, polymers of polystyrene, copolymers of polystyrene, copolymers of styrene and divinylbenzene, copolymers of dimethylacrylamide and N,N'-bisacryloylethylenediamine, soluble support medium or PEPS.

31. The process of claim 30, wherein said support medium is controlled pore glass, polymers of polystyrene or copolymers of polystyrene.

32. The process of claim 12, wherein $Z_1$ is trimethylsilyl, triethylsilyl, t-butyldimethylsilyl, t-butyldiphenylsilyl, triphenylsilyl, benzoylformyl, acetyl, chloroacetyl, dichloroacetyl, trichloroacetyl, trifluoroacetyl, pivaloyl, benzoyl, p-phenylbenzoyl, 9-fluorenylmethoxycarbonyl, levulinyl or acetoacetyl groups.

33. The process of claim 12, wherein $Z_2$ is 4,4'-dimethoxytrityl, monomethoxytrityl, 9-phenylxanthen-9-yl, 9-(p-methoxyphenyl) xanthen-9-yl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetyl, chloroacetyl, trichloroacetyl, trifluoroacetyl, pivaloyl, benzoyl, p-phenylbenzoyl, mesyl, tosyl, 4,4',4"-tris-(benzyloxy)trityl, 4,4',4"-tris-(4,5-dichlorophthalimido)trityl, 4,4',4"-tris(levulinyloxy)trityl, 3-(imidazolylmethyl)-4,4'-dimethoxytrityl, 4-decyloxytrityl, 4-hexadecyloxytrityl, 9-(4- octadecyloxyphenyl)xanthene-9-yl, 1,1-bis-(4-methoxyphenyl)-1'-pyrenyl methyl, p-phenylazophenyloxycarbonyl, 9-fluorenylmethoxycarbonyl, 2,4-dinitrophenylethoxycarbonyl, 4-(methylthiomethoxy) butyryl, 2-(methylthiomethoxymethyl)benzoyl, 2-(isopropylthiomethoxymethyl)benzoyl, 2-(2,4-dinitrobenzenesulphenyloxymethyl)benzoyl, or levulinyl groups.

34. The process of claim 12, wherein said monomeric subunit having an activated phosphorus group is a phosphoramidite, an H-phosphonate or a phosphate triester.

35. The process of claim 34, wherein said monomeric subunit is a phosphoramidite.

36. The process of claim 12, wherein $Z_1$ is an acid labile hydroxyl-protecting group.

37. The process of claim 14, wherein each of said further hydroxyl protecting groups is acid labile.

38. The process of claim 37, wherein said further hydroxyl protecting groups are removed by contact with an acid, wherein said acid is formic acid, acetic acid, chloroacetic acid, dichloroacetic acid, trichloroacetic acid, trifluoroacetic acid, benzenesulfonic acid, toluenesulfonic acid, or phenylphosphoric acid.

39. The process of claim 14, wherein said oligomeric compound is an oligonucleotide, modified oligonucleotide, oligonucleotide analog, oligonucleoside, oligonucleotide mimetic, hemimer, gapmer or chimera.

40. The process of claim 39, wherein said oligomeric compound is an oligonucleotide.

* * * * *

UNITED STATES PATENT AND TRADEMARK OFFICE
CERTIFICATE OF CORRECTION

PATENT NO. : 6,653,468 B1
DATED : November 25, 2003
INVENTOR(S) : Andrei P. Guzaev It is certified that error appears in the above-identified patent and that said Letters Patent is hereby corrected as shown below:

Title page,
Item [56], References Cited, OTHER PUBLICATIONS, "Nelson" reference, please insert -- solid -- between "versatile" and "support.".

Signed and Sealed this

Eighteenth Day of October, 2005

JON W. DUDAS
*Director of the United States Patent and Trademark Office*